(12) United States Patent
Li et al.

(10) Patent No.: US 7,250,296 B2
(45) Date of Patent: Jul. 31, 2007

(54) NUCLEOTIDE SEQUENCES OF 2S ALBUMIN GENE AND ITS PROMOTER FROM GRAPE AND USES THEREOF

(75) Inventors: Zhijian T. Li, Altamonte Springs, FL (US); Dennis J. Gray, Howey-in-the-Hills, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 425 days.

(21) Appl. No.: 10/382,066

(22) Filed: Mar. 5, 2003

(65) Prior Publication Data

US 2004/0177404 A1 Sep. 9, 2004

(51) Int. Cl.
C12N 15/82 (2006.01)
C12N 15/33 (2006.01)
A01H 5/00 (2006.01)

(52) U.S. Cl. ............... 435/419; 435/320.1; 435/252.3; 536/24.1; 536/23.72; 800/298

(58) Field of Classification Search ............. 435/320.1, 435/419; 536/24.1; 800/298
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,380,831 A | 1/1995 | Adang et al. | |
| 5,487,991 A | 1/1996 | Venderckhove et al. | |
| 5,567,600 A | 10/1996 | Adang et al. | |
| 5,567,862 A | 10/1996 | Adang et al. | |
| 5,589,615 A | 12/1996 | De Clerq et al. | |
| 5,623,067 A | 4/1997 | Vanderckhove et al. | |
| 5,986,174 A | 11/1999 | Barbour et al. | |
| 6,013,523 A | 1/2000 | Adang et al. | |
| 6,015,891 A | 1/2000 | Adang et al. | |
| 6,080,914 A | 6/2000 | Conner | |
| 6,395,964 B1 | 5/2002 | Antzen et al. | |

FOREIGN PATENT DOCUMENTS

WO WO 00/40710 * 7/2000

OTHER PUBLICATIONS

Abbal P. et al. GenBank Accession BQ792946, Jul. 30, 2002, Est 7851 Grape berries seeds Lambda TriplEx2 Library Vitis vinifera cDNA clone ST003G11 3', mRNA sequence.*
da Silva Conceicao A. et al. A cotyledon regulatory region is responsible for the different spatial expression patterns of Arabidopsis 2S albumin genes. Plant J. Apr. 1994;5(4):493-505.*
Kim Y et al. A 20 nucleotide upstream element is essential for the nopaline synthase (nos) promoter activity. Plant Mol Biol. Jan. 1994;24(1):105-17.*
da Pater S et al. A 22-bp fragment of the pea lectin promoter containing essential TGAC-like motifs confers seed-specific gene expression.Plant Cell. Aug. 1993;5(8):877-86.*
Database GENBANK, Accession No. AW707958; AGEORGES, A. "Grape berries Lambda Zap II Library Vitis vinifera cDNA clone A099 3' similar to albumin seed storage protein precursor from Juglans regia (U66866), MRNA sequence" (2000).
An, Y.Q., et al., "Strong, constitutive expression of the Arabidopsis ACT2/ACT8 actin subclass in vegetative tissues", *Plant J.* (1996), pp. 107-121, vol. 10.
Barciszewski, J., et al., "Minireview: analysis of rape seed napin structure and potential roles of the storage protein", *J. Protein Chem.* (2000), pp. 249-254, vol. 29.
Boutilier, K., et al., "Evolution of 2S albumin seed storage protein genes in the *Brassicaceae*" *BiochemSystem Ecol.* (1999), pp. 223-234, vol. 27.
Burrow, M.D., et al., "High frequency generation of transgenic tobacco plants after modified leaf disk cocultivation with *Agrobacterium tumefaciens*" *Plant Mol Biol Rep* (1990), pp. 153-168, vol. 8.
Chatthai, M. and Misra, S. "Sequence and expression of embryogenesis-specific cDNA encoding 2S seed storage proteins in *Pseudotsuga menziesii* (Mirb.) Franco" *Planta* (1998), pp. 138-145, vol. 206.
Conceição, A.S. and Krebbers, E. "A cotyledon regulatory region is responsible for the different spatial expression patterns of *Arabidopsis* 2S albumin genes" *Plant J.* (1994), pp. 493-505, vol. 5.
Corneille, S., et al., "Efficient elimination of selectable marker genes from the plastid genome by the CRE-*lox* site-specific recombination system" *Plant J.* (2001), pp. 171-178, vol. 27.
Dasgupta, S., et al., "Cloning and sequencing of 5' flanking sequence from the gene encoding 2S storage protein, from two *Brassica* species" *Gene* (1993), pp. 301-302, vol. 133.
De Lumen, B.O., et al, "Molecular strategies to improve nutritional quality of legume proteins", *Adv. Exp. Med. Biol.* (1999), pp. 117-126, vol. 464.
D'Halluin, K., et al., "The *bar* gene as selectable and screenable marker in plant engineering" *Methods Enzymol.* (1993), pp. 415-426, vol. 216.
Dharmapuri, S., et al., "Metabolic engineering of xanthophylls content in tomato fruits", *FEBS Lett.* (2002), pp. 30-34, vol. 519.

(Continued)

*Primary Examiner*—Cynthia Collins
(74) *Attorney, Agent, or Firm*—Saliwanchik, Lloyd & Saliwanchik

(57) ABSTRACT

The subject invention pertains to the isolation of nucleotide sequences of the 2S albumin gene and its promoter from grape. Promoter sequences of the invention provide for seed-specific transcription of operably linked polynucleotide sequences. Seed-specific expression activity of the subject promoter was also characterized by using transient green fluorescent protein (GFP) expression analysis in transformed somatic embryos (SE) of grape (cv. Thompson Seedless). The subject invention also concerns expression constructs comprising a promoter of the present invention. Plants, plant tissues, and plant cells bred to contain or transformed with a polynucleotide of the invention are also contemplated by the present invention.

28 Claims, 6 Drawing Sheets

OTHER PUBLICATIONS

Ezcurra, I., et al, "Transactivation of the *Brassica napus* napin promoter by AB13 requires interaction of the conserved B2 and B3 domains of AB13 with different *cis*-elements: B2 mediates activation through an ABRE, whereas B3 interacts with an RY/G-box", *Plant J.* (2000), pp. 57-66, vol. 24.

Fischer, R. and Emans, N. "Molecular farming of pharmaceutical proteins", *Transgenic Res.* (2000), pp. 279-299, vol. 9.

Galili, G. and Hofgen, R. "Metabolic engineering of amino acids and storage proteins in plants", *Meta Eng.* pp. 3-11, vol. 4.

Ger, M., et al., "Constitutive expression of hrap gene in transgenic tobacco plant enhances resistance against virulent bacterial pathogens by induction of a hypersensitive response", *Mol. Plant. Microbe. Interact.* (2002), pp. 764-773, vol. 15.

Gray, D.J., "Somatic embryogenesis and plant regeneration from immature zygotic embryos of muscadine grape (*Vitis rotundifolia*) cultivars", *Am. J. Bot.* (1992), pp. 542-546, vol. 79.

Guerche, P., et al., "Differential Expression of the *Arabidopsis* 2S Albumin Genes and the Effect of increasing Gene Family Size", *Plant Cell* (1990), pp. 469-478, vol. 2.

Hood, E.E. and Jilka, J.M. "Plant-based production of xenogenic proteins", *Curr Opin Biotechnol.* (1999), pp. 382-386, vol. 10.

Iamtham, S. and Day, A. "Removal of antibiotic resistance genes from transgenic tobacco plastids" *Nat Biotechnol.* (2000), pp. 1172-1176, vol. 18.

De Jaeger, G., et al., "Boosting Heterologous protein production in transgenic dicotyledonous seeds using *Phaseolus vulgaris* regulatory sequences", *Nat. Biotech.* (2002), pp. 1265-1268, vol. 20.

Klöti, A., et al., "Tissue-specific silencing of a transgene in rice", *Proc. Natl. Acad. Sci. USA* (2002), pp. 10881-10886, vol. 99.

Koo, J.C., et al., "Over-expression of a seed specific hevein-like antimicrobial peptide from *Pharbitis nil* enhances resistance to a fungal pathogen in transgenic tobacco plants", *Plant Mol Biol* (2002), pp. 441-452, vol. 50.

Li, Z., et al., "Use of marker genes to target disease resistance gene expression in grape" 10th IAPTC&B Congress, *Plant Biotechnology 2002 and Beyond*, Jun. 23-29, 2002, p. 58-A.

Li, Z., et al., "Expression of a bifunctional green fluorescent protein (GFP) fusion marker under the control of three constitutive promoters and enhanced derivatives in transgenic grape (*Vitis vinifera*)" *Plant Sci.* (2001), pp. 877-887, vol. 160.

Liu, Y.G. and Whittier, R.F. "Thermal asymmetric interlaced PCR: automatable amplification and sequencing of insert end fragments from P1 and YAC clones for chromosome walking" *Genomics* (1995), pp. 674-681, vol. 25.

Liu, Y.G. and Huang, N. "Efficient amplification of insert end Sequences from bacterial artificial chromosome clones by thermal asymmetric interlaced PCR" *Plant Mol Biol Rep.* (1998), pp. 175-181, vol. 16.

Lohdi, M.A., Yes, G.N., Weeden, N.F., Reisch, B.J. "A simple and efficient method for DNA extraction from grapevine cultivars and *Vitis* species" *Plant Mol. Biol. Rep.* (1994), pp. 6-13, vol. 12.

Longstaff, M., Brigneti, G., Boccard, F., Chapman, S., Baulaube, D. "Extreme resistance to potato virus X infection in plants expressing a modified component of the putative viral replicase" *EMBO J.* (1993), pp. 379-386, vol. 12.

Maniatis, T., Fritsch, E. F., Sambrook, J. *Molecular Cloning: A Laboratory Manual*, Cold Spring Harbor Laboratory (1982), Cold Spring Harbor, NY.

Maniatis, T., Fritsch, E. F., Sambrook, J. *Molecular Cloning: A Laboratory Manual*, 2d Edition, Cold Spring Harbor Laboratory (1989), Cold Spring Harbor, NY.

Molvig, L., Tabe, L. M., Eggum, B. O., Moore, A. E., Craig, S., Spencer, D., Higgins, T. J. "Enhanced methionine levels and increased nutritive value of seed of transgenic lupins (*Lupinus angustifolius* L.) expressing a sunflower seed albumin gene" *Proc Natl Acad Sci USA* (1997), pp. 8393-8398, vol. 94.

Müntz, K. "Deposition of storage proteins" *Plant Mol Biol* (1998), pp. 77-99, vol. 38.

Müntz, K., Christov, V., Saalbach, G., Saalbach, I., Waddell, D., Pickardt, T., Schieder, O., Wustenhagen, T. "Genetic engineering for high methionine grain legumes" *Nahrung* (1998), pp. 125-127, vol. 42.

Perlak, F. J., Deaton, R. W., Armstrong, T. A., Fuchs, R. L., Sims, S. R., Greenplate, J. T., Fischhoff, D. A. "Insect resistant cotton plants" *Biotechnology* (1990), pp. 939-943, vol. 8.

Raynal, M., Depigny, D., Grellet, F., Delseny, M. "Characterization and evolution of napin-encoding genes in radish and related crucifers" *Gene* (1991), pp. 77-86, vol. 99.

Rico M., Bruix, M., Gonzalez, C., Monsalve, R. I., Rodriguez, R. "H NMR assignment and global fold of napin Bnlb, a representative 2S albumin seed protein" *Biochem* (1996), pp. 15672-15682, vol. 35.

Roeckel, P., Oancia, T., Drevet, J. "Effects of seed-specific expression of a cytokinin biosynthetic gene on canola and tobacco phenotypes" *Transgenic Res* (1997), pp. 133-141, vol. 6.

Scarafoni, A., Carzaniga, R., Harris, N., Croy, R. R. "Manipulation of the napin primary structure alters its packaging and deposition in transgenic tobacco (*Nicotiana tabacum* L.) seeds" *Plant Mol Biol* (2001), pp. 727-739, vol. 46.

Shewry P. R., Napier, J. A., Tatham, A. S. "Seed storage proteins: structures and biosynthesis" *Plant Cell* (1995), pp. 945-956, vol. 7.

Stålberg, K., Elierström, M., Josefsson, L.G., Rask, L. "Deletion analysis of a 2S seed storage protein promoter of *Brassica napus* in transgenic tobacco" *Plant Mol Biol* (1993), pp. 671-683, vol. 23.

Tai, S.S.K., Lee, T.T.T., Tsai, C.C.Y., Yiu, T.J., Tzen, J.T.C. "Expression pattern and deposition of three storage proteins 11S globulin, 2S albumin and 7S globulin in maturing sesame seeds" *Plant Physiol Biochem* (2001), pp. 981-992, vol. 39.

Terauchi R, Kahl, G. "Rapid isolation of promoter sequences by TAIL-PCR: the 5'-flanking regions of *Pal* and *Pgi* genes from yarns (*Dioscorea*)" *Mol Gen Genet* (2000), pp. 554-560, vol. 263.

Terras, F. R. G., Torrekens, S., Van Leuven, F., Osbron, R. W., Vanderleyden, J., Cammue, B. P. A., Broekaert, W. F. "A new family of basic cysteine-rich plant antifungal proteins from Brassicaceae species" *FEBS Lett* (1993), pp. 233-240, vol. 316.

Teuber, S.S., Dandekar, A. M., Peterson, W. R., Sellers, C. L. "Cloning and sequencing of a gene encoding a 2S albumin seed storage protein precursor from English walnut (*Juglans regia*), a major food allergen" *J Allergy Clin Immunol* (1998), pp. 807-814, vol. 101.

Vincentz, M., Leite, A., Neshich, G., Vriend, G., Mattar, C., Barros, L., Weinberg, D., De Almeida, E. R., De Carvalho, M. P., Aragäo, F., Gander, E. S. "ACGT and vicilin core sequences in a promoter domain required for seed-specific expression of a 2S storage protein gene are recognized by the opaque-2 regulatory protein" *Plant Mol Biol.* (1997), pp. 879-889, vol. 34.

Wei, C. F. et al., "Isolation and Comparison of Two Molecular Species of the BAL 31 Nuclease from *Alteromonas espejiana* with Distinct Kinetic Properties" *J. Biol. Chem.* (1983), pp. 13506-13512, vol. 258, No. 22.

Yang, T. T. et al. "Optimized Codon Usage and Chromophore Mutations Provide Enhanced Sensitivity with the Green Fluorescent Protein" *Nucleic Acid Research* (1996), pp. 4592-4593, vol. 24, No. 22.

Zheng, Z., Kawagoe, Y., Xiao, S., Li, Z., Okita, T., Hau, T. L., Lin, A., Murai, N. "5' Distal and Proximal *Cis*-acting Regulator Elements are Required for Developmental Control of a Rice Seed Storage Protein *Glutelin* Gene" *Plant J.* (1993), pp. 357-366, vol. 4.

Zuo, J., Niu, Q. W., Moller, S. G., Chua, N. H. "Chemical-regulated, site-specific DNA excision in transgenic plants" *Nat Biotechnol.* (2001), pp. 157-161, vol. 19.

Li, Z.T. et al. "*Vitis vinifera* cultivar Merlot S albumin precursor (Alb1) gene, promoter region and complete cds" Database EMBL genomic DNA, 1164nt, May 8, 2003, XP002293811, Database accession No. AY267256.

Li, Z. T. et al. "*Vitis vinifera* cultivar Chardonnay 2S albumin precursor (Alb1) gene, promoter region and complete cds" Database EMBL genomic DNA, 691 nt, May 8, 2003, XP002293812, Database accession No. AY267254.

\* cited by examiner

```
  1  CGGAGGCTTA ATCCAGTTGA AGAGTGAAGG TTGGGCCGGA GCCTTACAGC CCAAATTGAG TTGGTGGGTT GGTGCTGAGA
     GCCTCCGAAT TAGGTCAACT TCTCACTTCC AACCCGGCCT CGGAATGTCG GGTTTAACTC AACCACCCAA CCACGACTCT

81  GGCTTGTGTT CAAAGTCCAT ATCCATTCGA AAAAATTTTG CCCTCTTGTA TAAGCCTCAG GAATCTCTTT AGCCTTTAAT
     CCGAACACAA GTTTCAGGTA TAGGTAAGCT TTTTTAAAAC GGGAGAACAT ATTCGGAGTC CTTAGAGAAA TCGGAAATTA

161  TAAACCTAAA TCCTACCAAA ACTGCCCTTC AAAATTATTG CTTTGTTTTA GGTCCAAGAA TCCTAAATAA GGTCTATTTT
     ATTTGGATTT AGGATGGTTT TGACGGGAAG TTTTAATAAC GAAACAAAAT CCAGGTTCTT AGGATTTATT CCAGATAAAA

241  GAAACATTCC TAATGGGGTG GGCTTTGCTT CTCCAAACAG AAGCATACTA CTTGCTGTTG ATGAGCATGT CTGTCACCTC
     CTTTGTAAGG ATTACCCCAC CCGAAACGAA GAGGTTTGTC TTCGTATGAT GAACGACAAC TACTCGTACA GACAGTGGAG

321  CAAAAAAAGG ACAAGGTAAC TTTAACTGCA GCATTAAATG TATAGGAAGC AGTATTACAA TCAAAATCAG TTTATGGCAG
     GTTTTTTTCC TGTTCCATTG AAATTGACGT CGTAATTTAC ATATCCTTCG TCATAATGTT AGTTTTAGTC AAATACCGTC
                           PstI
401  CCTTTCCATG AATGCTCCCA TTTCAGCATG CAAACTAACC CACACTAACC TCCACACGTC CACACCTCCC ACCATAAACC TGCCCTATCC
     GGAAAGGTAC TTACGAGGGT AAAGTCGTAC GTTTGATTGG GTGTGATTGG AGGTGTGCAG GTGTGGAGGG TGGTATTGG ACGGGATAGG
                                SphI
481  CCAGCCCACT TCCACGTACA CACCCCATGC AAGTCCTGGA CTTCACTATA AATAACTGCC CTTCATCCCC CTCTTCACTC
     GGTCGGGTGA AGGTGCATGT GTGGGGTACG TTCAGGACCT GAAGTGATAT TTATTGACGG GAAGTAGGGG GAGAAGTGAG
                                             TATA-box
                                                         M   A   K   L   S   I   F   A   A   T   L   L   L
561  ACTCATCATC GATCCCTCTC TCTCATTACA AAAAAACGAT GGCGAAGCTC TCAATTTTCG CAGCTACTCT CCTCCTCCTC
     TGAGTAGTAG CTAGGGAGAG AGAGTAATGT TTTTTTGCTA CCGCTTCGAG AGTTAAAAGC GTCGATGAGA GGAGGAGGAG
     ClaI
```

FIG. 2A

```
      L   A   I   S   N   A       T   I   Y   Q       T   T   V       I   T   R       D   D   G   S       E   F   G       Q   F   Q
 641  CTAGCCATCT CCAACGCCAC CATCTACCAA ACCACCGTCA TCACCAGGGA TGATGGGTCC GAATTTGGGC AGTTCCAGGG
      GATCGGTAGA GGTTGCGGTG GTAGATGGTT TGGTGGCAGT AGTGGTCCCT ACTACCCAGG CTTAAACCCG TCAAGGTCCC
      G   S   Q   S       Q   R   C       Q   Q       I   Q   G   Q       F   Q       Q   C   E       R   Y   I   R       Q   Q   A
 721  GAGCCAGAGC CAGAGGTGCA GGCAGCAGAT ACAAGGCCAG CAGTTCCAGC AGTGCGAACG GTACATTAGG CAGCAAGCGG
      CTCGGTCTCG GTCTCCACGT CCGTCGTCTA TGTTCCGGTC GTCAAGGTCG TCACGCTTGC CATGTAATCC GTCGTTCGCC
      E   Q   Q   Q       G   G   Q       G   D   V       L   I   L   R       G   I   R       N   Q   Q       Q   Q   E   Q       Q   W   L
 801  AGCAACAGCA GGGCGGGCAG GGTGACGTAC TGATTTTACG GGGCATCAGA AACCAGCAAC AACAGGAACA GCAATGGCTC
      TCGTTGTCGT CCCGCCCGTC CCACTGCATG ACTAAAATGC CCCGTAGTCT TTGGTCGTTG TTGTCCTTGT CGTTACCGAG
      R   Q   C       C   Q   A   L       Q   N   M       D   Q   Q       C   Q   C   E       G   L   R       Q   I   V       Q   R   Q   Q
 881  CGCCAGTGCT GCCAAGCGTT GCAGAACATG GATCAGCAAT GCCAGTGTGA GGGTCTCCGC CAGATAGTGC AAAGGCAGCA
      GCGGTCACGA CGGTTCGCAA CGTCTTGTAC CTAGTCGTTA CGGTCACACT CCCAGAGGCG GTCTATCACG TTTCCGTCGT
      G   Q   G   Q       G   G   Q       G   Q   G   Q       R   E   Q       Q   Q   E       M   M   Q   I       A   Q   K
 961  GGGTCAGGGT CAGGGTCAGG GACAGGGACA CAGAGAGAGC CAGAGCAGGA GATGATGCAG ATAGCACAGA
      CCCAGTCCCA GTCCCAGTCC CTGTCCCTGT GTCTCTCTCG GTCTCGTCCT CTACTACGTC TATCGTGTCT
      L   P   E       R   C   G   S       G   Q   A       C   Q   S       M   Q   V   V       W   F   *
1041  AGCTGCCGGA AAGGTGCGGC TCCGGACAAG CCTGCCAGAG CATGCAAGTT GTCTGGTTCT AGGGCTTTTG CAGGCGGTGTT
      TCGACGGCCT TTCCACGCCG AGGCCTGTTC GGACGGTCTC GTACGTTCAA CAGACCAAGA TCCCGAAAAC GTCGCCACAA
                                                              SphI
1121  GATAATAAAG TTCAATCACT TAGGGTGACT GGAAACGAGT AACA
      CTATTATTTC AAGTTAGTGA ATCCCACTGA CCTTTGCTCA TTGT
```

NUCLEOTIDE SEQUENCES OF 2S ALBUMIN GENE AND ITS PROMOTER FROM GRAPE AND USES THEREOF

BACKGROUND OF THE INVENTION

Promoters regulate gene transcription and provide sophisticated controlling mechanisms for gene expression. Based on their functionality, promoters can be generally grouped into tissue-specific promoters, developmentally regulated promoters, constitutive promoters and inducible promoters. Tissue-specific promoters become functionally active only in a particular type of cell, tissue or organ, while developmentally regulated promoters mainly function at a certain stage of plant development. Constitutive promoters, on the other hand, are active in all types of tissues and at all stages of plant development, providing a relatively constant level of gene expression. Lastly, inducible promoters, increase activity greatly when they come in contact with associated chemical or physical signals. Thus far, numerous promoters with a wide range of functionalities have been isolated from organisms ranging from viruses to plants to mammals. These promoters are potentially important for the successful application of genetic engineering techniques to crop plants in efforts to introduce resistance characteristics to biotic and abiotic stresses, to improve crop yield and quality, and to create novel traits with added value.

Currently, the majority of promoters being successfully utilized in plant genetic engineering are mainly derived from a few plant viruses, including cauliflower mosaic virus (CaMV) and cassava vein mosaic virus (CsVMV). These viral promoters tend to support strong and often constitutive transgene expression in plant cells (Li et al., 2001). Hence, they are normally used for expressing selectable marker genes to facilitate the selection and identification of transgenic plants. In addition, due to their unusually stable and high-level of activity, these promoters are often used to drive expression of transgenes such as those conferring resistance to disease pathogens, insects and herbicides (D'Halluin et al., 1993; Lonstaff et al., 1993; Perlak et al., 1990; Ger et al., 2002). However, viral promoters generally lack the capability to promote tissue-specific expression and some show unpredictable expression patterns in different host plants (Li et al., 2001; Kloti et al., 2002). In addition to viral promoters, several promoters isolated from plants have also been successfully used in genetic engineering programs (An et al., 1996; Dharmapuri et al., 2002). These plant-derived promoters are capable of supporting tissue-specific and developmentally-regulated transgene expression, but more often display unexpected changes in promoter activity and expression patterns in heterologous host plants (Li et al., 2001). The use of plant-derived promoters for efficient transgene expression has been somewhat under-exploited. More needs to be done in the discovery, isolation and characterization of novel plant-derived promoters from different plant species and in the utilization of these promoters in order to diversify and enhance our ability to achieve effective transgene expression in transgenic plants.

Promoters are a key component in the application of genetic engineering techniques aimed at improving the survivability and value of crop plants. In spite of tremendous efforts made to isolate and characterize promoters from various sources, the number of promoters capable of providing a strong and tissue-specific activity in a particular host plant is still limited mainly due to the sophisticated mechanisms employed by different promoters to control gene expression (Li et al., 2001). Thus, there is a great need for discovery and exploration of new promoters in order to diversify our approach to supporting transgene expression in various plant species for different purposes.

2S albumins are a group of small proteins (1.7 to 2.2S) synthesized and stored in plant seeds of a wide range of dicotyledonary species and are well known for their conserved pattern of placement of cysteine residues that are involved in disulphide bond formation (Shewry et al., 1995; Rico et al., 1996). These proteins vary greatly in amino acid composition but often contain a high percentage of nitrogen- and sulfur-rich amino acid residues consistent with significant nutritional functions of storage proteins (Boutilier et al., 1999). Due to their important role as a nutritional supply source for human food and animal feeds, 2S albumins and associated genes have been isolated from a number of plant species and characterized in great detail to facilitate endeavors in protein manipulation and improvement (Raynal et al., 1991; Shewry et al., 1995; Rico et al., 1996; Cahtthai and Misra 1998; Muntz 1998; Scarafoni et al., 2001; Galili and Hofgen 2002). Several glutamine (Q)-rich 2S albumins have also been shown to possess potent antimycotic and antibacterial activities. These proteins provide useful characteristics for the development of novel disease resistance in crop plants using transgenic strategies (Terras et al., 1993; Barciszewski et al., 2000; Koo et al., 2002).

The production and accumulation of 2S albumins during seed development are strictly controlled by their gene promoters. Over the years, extensive molecular analysis of 2S albumin promoters from different plant species revealed that several unique DNA motifs within these promoters interact directly with well-characterized transcriptional regulatory proteins leading to spatial and temporal activation of gene transcription (Dasgupta et al., 1993; Stalberg et al., 1993; Conceicao and Krebbers 1994; Rockel et al., 1997; Vincentz et al., 1997). Knowledge gained from these studies greatly facilitated efforts to improve yield, quality and nutritional value of seed storage proteins by using genetic engineering techniques (Molvig et al., 1997; Muntz et al., 1998; De Lumen et al., 1999; Scarafoni et al., 2001; Jaeger et al., 2002).

A cDNA clone from a grape berry library of cv. Pinor Noir was published previously in the form of an expressed sequence tag (EST) (Ageorges 2000). This partial cDNA was shown to have sequence homology to a gene encoding a 2S albumin seed storage protein precursor from *Juglans regia* (U66866) and thus was proposed to belong to a 2S albumin-like gene in grape. Although the isolation and utilization of 2S albumin genes and promoters from other species has been disclosed in the art, none have sequence homology to the gene and promoter of the subject invention (Arntzen et al., 2002; Vandekerckhove et al., 1997; De Clercq et al., 1996; Vandekerckhove et al., 1996).

BRIEF SUMMARY OF THE INVENTION

The subject invention pertains to the isolation of nucleotide sequences of the 2S albumin gene and its promoter from grape (*Vitis* sp.). Seed-specific expression activity of the subject promoter was also characterized by using transient green fluorescent protein (GFP) expression analysis in transformed somatic embryos (SE) of grape (cv. Thompson Seedless). The subject invention also concerns expression constructs comprising a promoter of the present invention. Plants, plant tissues, and plant cells bred to contain or transformed with a polynucleotide of the invention are also contemplated by the present invention.

BRIEF DESCRIPTION OF THE FIGURES

FIG. 2 shows a compiled DNA sequence of 2S albumin gene and its promoter from grape cv. Merlot. Deduced amino acid residues are produced by Vector NTI DNA analysis software.

BRIEF DESCRIPTION OF THE SEQUENCES

Figure 1:
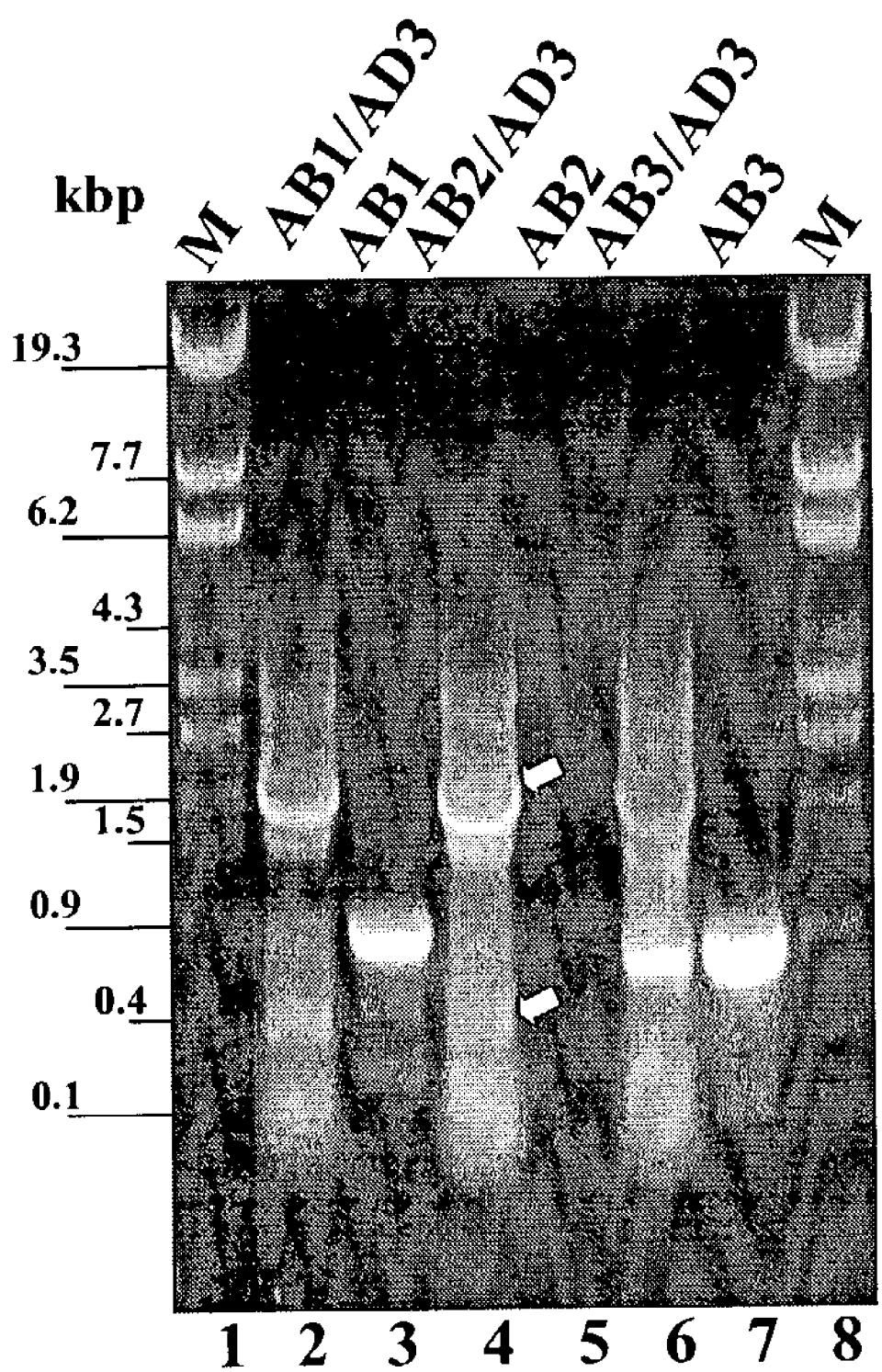
FIG. 1 shows an agarose gel analysis of TAIL-PCR products using a modified procedure and grape genomic DNA (*V. vinifera* cv. Merlot). Primers AB1, AB2, and AB3 were synthesized based on grape EST (AW707958). AD3 is a degenerate arbitrary primer. Arrows indicate fragments that were isolated and cloned for subsequent DNA sequencing.

SEQ ID NO. 1 is a nucleotide sequence of a 2S albumin gene of *V. vinifera* cv. Merlot.

SEQ ID NO. 2 is nucleotides 6 through 592 of SEQ ID NO. 1 which comprises the promoter of the 2S albumin gene of *V. vinifera* cv. Merlot.

SEQ ID NO. 3 is a nucleotide sequence of a 2S albumin gene of *V. vinifera* cv. Thompson Seedless.

SEQ ID NO. 4 is a nucleotide sequence of a 2S albumin gene of *V. vinifera* cv. Chardonnay clone 1.

SEQ ID NO. 5 is a primer sequence that can be used according to the present invention.

SEQ ID NO. 6 is a primer sequence that can be used according to the present invention.

SEQ ID NO. 7 is a primer sequence that can be used according to the present invention.

SEQ ID NO. 8 is a primer sequence that can be used according to the present invention.

SEQ ID NO. 9 is a primer sequence that can be used according to the present invention.

SEQ ID NO. 10 is a primer sequence that can be used according to the present invention.

SEQ ID NO. 11 is a primer sequence that can be used according to the present invention.

SEQ ID NO. 12 is a primer sequence that can be used according to the present invention.

SEQ ID NO. 13 is a fragment of SEQ ID NO. 2 that can be used according to the present invention.

SEQ ID NO. 14 is a fragment of SEQ ID NO. 2 that can be used according to the present invention.

SEQ ID NO. 15 is a fragment of SEQ ID NO. 2 that can be used according to the present invention.

SEQ ID NO. 16 is a fragment of SEQ ID NO. 2 that can be used according to the present invention.

SEQ ID NO. 17 is a fragment of SEQ ID NO. 2 that can be used according to the present invention.

SEQ ID NO. 18 is a fragment of SEQ ID NO. 2 that can be used according to the present invention.

SEQ ID NO. 19 is a fragment of SEQ ID NO. 2 that can be used according to the present invention.

SEQ ID NO. 20 is a fragment of SEQ ID NO. 2 that can be used according to the present invention.

SEQ ID NO. 21 is a fragment of SEQ ID NO. 2 that can be used according to the present invention.

SEQ ID NO. 22 is a fragment of SEQ ID NO. 2 that can be used according to the present invention.

SEQ ID NO. 23 is a fragment of SEQ ID NO. 2 that can be used according to the present invention.

SEQ ID NO. 24 is a fragment of SEQ ID NO. 2 that can be used according to the present invention.

SEQ ID NO. 25 is a fragment of SEQ ID NO. 2 that can be used according to the present invention.

SEQ ID NO. 26 is a fragment of SEQ ID NO. 2 that can be used according to the present invention.

SEQ ID NO. 27 is a fragment of SEQ ID NO. 2 that can be used according to the present invention.

SEQ ID NO. 28 is a fragment of SEQ ID NO. 2 that can be used according to the present invention.

SEQ ID NO. 29 is an amino acid sequence of a 2S albumin protein of *V. vinifera* cv. Merlot encoded by a nucleotide sequence of SEQ ID NO. 1.

DETAILED DISCLOSURE OF THE INVENTION

The subject invention concerns the isolation and cloning of grape 2S albumin gene, and in particular, a polynucleotide promoter sequence of the 2S albumin gene that provides for seed-specific transcription of an operably linked polynucleotide sequence. In a specific embodiment, the promoter is from the 2S albumin gene of *V. vinifera* cv. Merlot. The subject promoter is fully functional in grape cotyledonary tissue and is also capable of promoting high levels of transgene expression comparable to the levels achieved using an enhanced viral promoter in grape somatic embryos (SE). A promoter of the present invention can also be used to drive seed-specific transgenic expression in other plant species (Conceicao and Krebbers 1994). As used herein, "promoter" or "promoter sequence" means a polynucleotide sequence of a nucleic acid molecule that is capable of directing an RNA polymerase to initiate transcription (i.e., the synthesis of RNA on a DNA template) at a transcription initiation site.

The isolation of seed tissue-specific 2S albumin gene promoter sequences from grape adds a unique and important tool in efforts to genetically engineer this and other crops. For instance, a promoter of the present invention can be used to drive expression of a selectable marker gene in seed-related transformation explants such as SE of grape to allow the outgrowth of the relatively few transformed cells among the vast majority of non-transformed cells, and facilitate the subsequent recovery and development of transgenic plants. Promoters of the present invention become inactive at the developmental stages of plant growth leading to and including a whole plant due to the tightly controlled tissue-specific expression pattern encoded within the promoter sequence. Accordingly, the selectable marker gene(s) will cease expression and no marker protein(s) will be produced in non-seed cell types. The marker gene(s) will essentially be turned into non-functional DNA, similar to the vast non-sense DNA present throughout the plant genome. Transgenic plants containing such a conditionally inactive selectable marker gene system will no longer require the physical removal of marker gene sequences by cumbersome procedures and techniques (Iamtham and Day 2000; Corneille et al., 2001; Zuo et al., 2001). The removal of active marker genes from transgenic plants was originally deemed desirable in order to minimize the dissemination of selective proteins to the environment and their subsequent transfer to insects and microorganisms that might ultimately result in a threat to human health.

The promoters of the present invention also provide another important element for boosting production of transgenic proteins using seeds as a target. Seeds accumulate a large amount of storage protein to secure the survival of seedlings. This unusual protein synthesis and packaging capability of seeds has been long and widely recognized as an ideal system for the manufacturing of desired proteins, such as those with improved nutritive, industrial and pharmaceutical values (Fischer and Emans 2000; Hood and Jilka 1999). A promoter enhancement technology involving the use of a bi-directional arrangement of multiple enhancers and core promoters for increasing promoter activity and usability has been described in the art (Li et al., 2002). The expression activity of a promoter of the present invention can be enhanced when combined with this promoter enhancement technology. An enhanced seed-specific promoter of the invention can provide economic and commercial benefit in modem molecular farming programs that are based on the use of seeds as protein manufacturing apparatuses (Hood and Jilka 1999) and in the genetic engineering of crop plants involving the modification of seed characteristics (de Lumen et al., 1999).

In a preferred embodiment, a promoter of the invention comprises one of the nucleotide sequences shown in SEQ ID NO. 2, 3, or 4, or a fragment or variant thereof that can drive transcription of a polynucleotide sequence operably linked to the promoter sequence. In an exemplified embodiment, a promoter of the invention comprises the polynucleotide sequence shown in SEQ ID NO. 2. The promoter can be operably linked with a polynucleotide sequence encoding a polypeptide other than 2S albumin. The operably linked polynucleotide sequence can comprise a sequence encoding a protein, or an antisense sequence, or another polynucleotide sequence of interest. The promoter and polypeptide encoding sequence can be incorporated into a polynucleotide vector or construct for transforming plant cells.

The subject invention also concerns polynucleotide expression constructs that comprise a promoter sequence of the present invention operably linked to a structural gene sequence (encoding a protein), an antisense sequence, or other polynucleotide sequences of interest. In a preferred embodiment, the promoter comprises one of the nucleotide sequences shown in SEQ ID NO. 2, 3, or 4, or a fragment or variant thereof that can drive transcription of the operably linked sequence. The structural gene can be a gene encoding a plant protein or a gene encoding a protein from an organism other than a plant, for example, a human, mammal, insect, bacteria, or virus. Proteins that can be encoded by a gene sequence include, but are not limited to, enzymes, hormones, cytokines, interleukins, receptors, growth factors, immunoglobulins, transcription factors, and *Bacillus thuringiensis* (*B.t.*) crystal toxin proteins. Sequences encoding *B.t.* proteins which have codon usage for preferential expression in plants are described in U.S. Pat. Nos. 5,380,831; 5,567,862; 5,567,600; 6,013,523; and 6,015,891. If the gene is a plant gene, it can be a gene homologous to grape or heterologous to grape. The protein encoded by the gene can also be a chimeric protein, wherein the protein is composed of regions from two or more different proteins, or it can be a fusion protein, wherein the protein is composed of two or more different proteins fused in one contiguous sequence. An antisense sequence is a sequence wherein the RNA transcribed from the antisense sequence is at least partially complementary to RNA transcribed from a gene encoding a protein. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. Thus, a promoter sequence "operably linked" with a protein coding or antisense sequence are linked in such a manner that the promoter can direct the transcription of the protein coding or antisense sequence.

A promoter of the invention can be ligated to the protein encoding or antisense sequence of a polynucleotide using standard techniques known in the art. A single copy or multiple copies of a promoter of the present invention can be used with an operably linked protein encoding or antisense sequence in an expression construct of the invention. For example, multiple copies of a promoter comprising a nucleotide sequence of SEQ ID NO. 2, 3, or 4 can be operably linked in an expression construct.

A transcription start site is typically included in the expression construct. In a preferred embodiment, the promoter can be positioned about the same distance from the transcription start site as it is from the transcription start site in its natural genetic environment. Some variation in this distance is permitted without substantial decrease in promoter activity. For expression in plants, in addition to a promoter of the present invention, expression constructs of the invention may optionally contain a transcription termination sequence, a translation termination sequence, and/or enhancer elements. Transcription termination regions that can be used in an expression construct of the invention include, but are not limited to, octopine synthase or nopaline synthase 3' terminator regions, which can be positioned downstream of a coding sequence to provide for efficient termination. The termination region may be obtained from a 2S albumin gene sequence or may be obtained from different genes. Enhancer elements that increase activity of a promoter can also be included in the expression construct. Enhancer elements are known in the art, and include, but are not limited to, the 35S enhancer element, maize shrunken-1 enhancer element, and the SV40 enhancer element. A promoter of the present invention, or a fragment or variant thereof, can also be operably linked with any polynucleotide sequences, either homologous to grape or heterologous to grape, that provide cis-acting regulatory functions to boost or regulate promoter activity. For example, positive regulatory elements located in a region −5.1 to −1.8 kb upstream of the transcription start site have been identified with a gene encoding the seed storage protein Glutelin in rice (Zheng et al., 1993).

DNA sequences which direct polyadenylation of the mRNA encoded by the structural gene can also be included in the expression construct and include, but are not limited to, an octopine synthase or nopaline synthase signal. The expression constructs of the invention can also include a polynucleotide sequence that directs transposition of other genes, i.e., a transposon.

Expression constructs can also include one or more dominant selectable marker genes, including, for example, genes encoding antibiotic resistance and/or herbicide-resistance for selecting transformed plant cells. Antibiotic-resistance genes can provide for resistance to one or more of the following antibiotics: hygromycin, kanamycin, bleomycin, G418, streptomycin, paromomycin, neomycin, and spectinomycin. Herbicide-resistance genes can provide for resistance to phosphinothricin acetyltransferase or glyphosate.

Other markers used for plant cell transformation screening include genes encoding β-glucuronidase (GUS), luciferase, green fluorescence protein (GFP), or enhanced GFP (Yang et al., 1996).

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. A number of vectors are available for expression and/or cloning, and include, but are not limited to, pBR322, pUC series, M13 series, and pBLUESCRIPT vectors (Stratagene, La Jolla, Calif.).

Also contemplated within the scope of the present invention are fragments of a promoter sequence of the invention that can promote expression of an operably linked gene or antisense sequence. Fragments can be prepared by deleting nucleotides from either the 5' end, the 3' end, or both the 5' and 3' ends of the promoter sequence using techniques well known in the art. For example, fragments of a polynucleotide can be obtained by digestion with exonucleases, such as Bal 31 (Wei et al., 1983) and ExoIII, or restriction enzymes, such as EcoRI. Fragments encompassed within the scope of the subject invention include fragments of SEQ ID NOS. 2, 3, or 4, wherein n nucleotides are deleted from the 5', the 3' end, or the 5' and 3' end of the sequence and wherein n=any integer from 1 to about 560. Preferably, a fragment will comprise at least about 50 contiguous nucleotides of the full length promoter sequence. Even more preferably, the fragment will comprise at least about 100 contiguous nucleotides. Even more preferably, a fragment will comprise from at least about 200 contiguous nucleotides and, most preferably, from at least about 300 contiguous nucleotides, at least about 400 contiguous nucleotides, or at least about 500 contiguous nucleotides of the full length promoter sequence. A fragment of a 2S albumin promoter of the invention can comprise at least about 25, 50, 75, 100, 125, 150, 175, 200, 250, 300, 350, 400, 450, 500, or 550 nucleotides, or up to the number of nucleotides present in a full-length promoter sequence of the invention, for example 587 nucleotides for SEQ ID NO. 2. Exemplified herein are fragments having 25, 50, 75, 100, 150, and 200 nucleotides deleted from the 5' end of SEQ ID NO. 2 (see SEQ ID NOs. 13 to 18) or deleted from the 3' end of SEQ ID NO. 2 (see SEQ ID NOs. 19 to 24). Also exemplified are fragments having 25, 50, 75, and 100 nucleotides deleted from both the 5' and 3' end of SEQ ID NO. 2 (see SEQ ID NOs. 25 to 28). Preferably, a fragment will comprise a "TATA" box or recognition motif or can be modified to contain one.

Methods of identifying whether a fragment of a promoter is capable of initiating gene transcription are well known in the art. U.S. Pat. Nos. 6,080,914 and 5,986,174 provide assay systems that can be used for analysis of promoter fragments for activity.

The subject invention also concerns biologically-active variants of promoter sequences of the present invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

The subject invention also concerns cells transformed with a polynucleotide comprising a promoter sequence of the present invention. In a preferred embodiment, the cell is transformed with a polynucleotide comprising one of the nucleotide sequences shown in SEQ ID NO. 2, 3, or 4, or a fragment or variant thereof that can drive transcription of a polynucleotide sequence operably linked to the promoter sequence. Preferably, the promoter sequence is provided in an expression construct of the invention. The transformed cell can be a prokaryotic cell, for example, a bacterial cell, or the transformed cell can be a eukaryotic cell, for example, a plant or animal cell.

The subject invention also concerns polynucleotide probes that can hybridize with a nucleotide sequence of a plant 2S albumin gene. A probe can comprise all of a promoter sequence of the present invention, or fragments or variants thereof that can specifically hybridize to a nucleotide sequence of a plant 2S albumin gene, or a messenger RNA transcribed therefrom. Probes of the invention can be composed of at least about 7-10 nucleotides, or at least about 11-20 nucleotides, or at least about 21-30 nucleotides, or 31 or more nucleotides. Probes of the invention can also be used as polymerase chain reaction (PCR) primers to amplify plant 2S albumin gene sequences using PCR methods.

The subject invention also concerns methods for detecting a nucleotide sequence of a 2S albumin gene using a probe of the invention. The polynucleotide probes of the subject invention can be used according to standard procedures and conditions to specifically and selectively detect polynucleotide sequences that have sufficient homology to hybridize with the probe. Nucleic acid can be isolated from an organism using standard techniques known in the art and the isolated nucleic acid can be screened for hybridization with probes of the invention. Optionally, the nucleic acid can be subject to PCR amplification using suitable PCR primers. PCR amplification methods are known in the art and have been described in U.S. Pat. Nos. 4,683,195; 4,683,202; and 4,800,159. Various degrees of stringency can be employed during the hybridization. The degree of stringency can be controlled by temperature, ionic strength, pH, and the presence of denaturing agents such as formamide during hybridization and washing. Typically, probe hybridization is carried out under "stringent" conditions, as described herein. Hybridization methods and conditions are known in the art and are generally described in *Nucleic Acid Hybridization: A Practical Approach* (Hames, B. D., S. J. Higgins, eds.), IRL Press (1985) and Maniatis et al. (1989).

The probes and primers of the invention can also be used to identify and isolate related albumin gene sequences from other organisms and such related sequences are encompassed within the scope of the invention. PCR and hybridization methods are typically used for identifying and isolating related sequences.

Polynucleotides of the subject invention, including probes and primers, can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz, G. A. et al., 1983):

$$Tm=81.5\ C+16.6\ Log[Na+]+0.41(\%\ G+C)-0.61(\%\ formamide)-600/length\ of\ duplex\ in\ base\ pairs.$$

Washes are typically carried out as follows:
(1) Twice at room temperature for 15 minutes in 1×SSPE, 0.1% SDS (low stringency wash).
(2) Once at Tm-20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

The subject invention also concerns methods for promoting seed specific transcription and expression of a polynucleotide by transforming a plant, plant tissue or a plant cell with a nucleic acid comprising a promoter of the present invention operably linked with a polynucleotide, such as a polynucleotide encoding a protein, or an antisense sequence, or another polynucleotide sequence of interest. In a preferred embodiment, a promoter of the invention operably linked to a polynucleotide is provided in the form of an expression construct of the present invention. A plant or plant tissue can be regenerated from the transformed cell and the polynucleotide operably linked to the promoter can be expressed in seed tissue. Methods for transforming a plant, plant tissue, or a plant cell with a nucleic acid are known in the art and include, for example, Agrobacterium infection, biolistic methods, electroporation, calcium chloride treatment, etc. If the polynucleotide encodes a protein, the protein can be expressed in the cells of a plant or plant tissue regenerated from the transformed cell. Methods for regenerating a plant or plant tissue from a transformed cell are also known in the art.

Plants, plant tissues, and plant cells bred to contain or transformed with a polynucleotide of the invention are also contemplated by the present invention. Plants within the scope of the present invention include monocotyledonous plants, such as rice, wheat, barley, oats, sorghum, maize, sugarcane, pineapple, onion, bananas, coconut, lilies, grasses, and millet; and dicotyledonous plants, such as peas, alfalfa, tomato, melon, chickpea, chicory, clover, kale, lentil, soybean, tobacco, potato, sweet potato, radish, cabbage, rape, apple trees, grape, cotton, sunflower, thale cress, and lettuce; and conifers. Techniques for transforming plant cells with a gene are known in the art and include, for example, Agrobacterium infection, biolistic methods, electroporation, calcium chloride treatment, etc. Transformed cells can be selected, redifferentiated, and grown into plants using standard methods known in the art. The progeny of any transformed plant cells or plants are also included within the scope of the present invention.

MATERIALS AND METHODS

Plant Materials and DNA Preparation.

Somatic embryos (SE) of grape (*V. vinifera* L. cv. Thompson Seedless) were initiated from in vitro shoot-tip cultures and anthers as described previously (Gray 1992, 1995; Li et al., 2001). SE at the mid-cotyledonary stage of development were collected and utilized in transient expression analysis after *Agrobacterium*-mediated transformation according to Li et al. (2001).

Total genomic DNA was isolated from young leaves of greenhouse-grown plants (*V. vinifera* L. cvs. Thompson Seedless, Chardonnay and Merlot) according to the procedures of Lodhi et al. (1994) with increased EDTA concentration (100 mM) in the extraction buffer, and directly used in PCR-mediated DNA amplifications.

Thermal Asymmetric Interlaced PCR (TAIL-PCR).

All PCR reactions were performed using a PTC-100 Programmable Thermal Controller (MJ Research, Inc., Watertown Mass., USA). Regular Taq polymerase was purchased from Promega (Madison, Wis., USA). Standard procedures for DNA manipulation and cloning were followed (Maniatis et al., 1982). PCR products were electrophoretically separated in 0.80% agarose. DNA sizes were determined using Kodak 1D image analysis software (Eastman Kodak Co., New York, USA). DNA fragments were isolated from agarose gels, purified using Ultrafree-MC filter devices (Millipore Corp. Mass., USA) and ligated into pGEM-T vector (Promega, Madison, Wis., USA). The DNA sequence of insert fragments was determined by nucleotide sequencing using 3 to 4 randomly selected clones from each ligation reaction.

In this study, two phases of TAIL-PCR were carried out. The first TAIL-PCR utilized the same procedure as described by Liu and Huang (1998) with two nested gene-specific (NGS) primers TUS-1 (5'-TTCCTGTTGTTGCT-GCTGGTTTCGGATG-3') (SEQ ID NO. 5) and TUS-2 (5'-ATCAGTACGTAACCCTGCCCGC-3') (SEQ ID NO. 6). These two primers correspond to nucleotide positions +10 to +31 and +41 to +66, respectively, of a published expressed sequence tag (EST) clone AW707958 (Ageorges, 2000) previously isolated from a berry cDNA library of grape (*V. vinifera* cv. Pinot Noir). This EST clone has a high sequence homology to the 2S albumin seed storage protein precursor mRNA of English walnut (*Juglans regia* L., GenBank accession No. U66866) (Teuber et al., 1998). A total of 8 arbitrary degenerate (AD) primers were tested in the first round of TAIL-PCR, including four (AD1 to AD4) from Liu and Huang (1998) and four others (AP103, AP122, AP138 and AG140) from Terauchi and Kahl (2000).

For the second phase TAIL-PCR, three NGS primers including:

```
AB-1  (5'-TAATGAGAGAGAGGGATCGA-3');   (SEQ ID NO. 7)
AB-2  (5'-GGATGAAGGGCAGTTATTTA-3');   (SEQ ID NO. 8)
and
AB3   (5'-GCATGGGGTGTGTACGTGGAAG-3')  (SEQ ID NO. 9)
``` were synthesized based on PCR-extended DNA sequence 5' upstream of the EST sequence after the first phase TAIL-PCR. A randomly selected AD primer AD3 (5'-WGTGNAG-WANCANAGA-3', where W represents A or T, and N represents an A, T, G or C) (SEQ ID NO. 10) (Liu and Huang 1998) was employed in this phase of PCR amplifications.

After the second phase TAIL-PCR, the entire 2S albumin gene and its 5' upstream region were re-amplified from genomic DNA of several grape genotypes using a forward primer GTU-51 (5'-CCTATCCCCAGCCCACTTCCAC-3') (SEQ ID NO. 11) and a reverse primer TSA-33 (5'-TGT-TACTCGTTTCCAGTCAC-3') (SEQ ID NO. 12) and manufacturer's (Promega) recommended PCR conditions. These two primers were synthesized based on sequences of the amplified 5' upstream region and the available downstream EST sequence of the 2S albumin gene. Two to three pGEM-T-derived clones, each containing an amplified gene fragment from a single genotype, were chosen for subsequent sequencing and analysis.

Construction of Transformation Vectors and *Agrobacterium*-Mediated Transformation.

A 587 bp DNA fragment (nucleotides −594 to −7) (SEQ ID NO. 2) from the upstream region relative to the ATG start codon of the 2S albumin gene (SEQ ID NO. 1) was isolated from cloned PCR-derived DNA and end-modified to form a HindIII-KpnI fragment using PCR. This fragment was then used to replace the double-enhanced CsVMV promoter in a previously described transformation vector pDCsVM (Li et al., 2001). The resultant vector, designated pAL, contained a bi-functional EGFP-NPTII fusion gene under the control of the 587 bp fragment upstream of the 2S albumin gene and the termination site and polyadenination signal of the CaMV 35S transcript. The transformation vector was introduced into *A. tumefaciens* strain EHA105 as described by Li et al. (2001).

Procedures and culture media for *Agrobacterium*-mediated transformation of grape SE were essentially the same as described previously (Li et al., 2001). Following transformation, SE were kept in the dark for 2 days, washed, and subjected to one week culture in the dark prior to subsequent transgene expression analysis. GFP expression in transformed SE was monitored using a dissecting stereomicroscope equipped with a fluorescence illuminator and a GFP filter set (Leica Microscopy System Ltd., Heerbrugg, Switzerland). Transformation of leaf tissues of grape and tobacco (*Nicotiana tabacum* cv. Samson) was performed according to Burrow et al. (1990).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Isolation of Target Gene and its Promoter

Thermal asymmetric interlaced polymerase chain reaction (TAIL-PCR) was previously developed by Liu and Whittier (1995) for genomic walking using cloned large DNA fragments as template. Changes were made to improve the amplification efficiency and target specificity. These changes included 1) reducing the concentration of NGS primers from 2 µM to 0.2 µM; 2) increasing the concentration of AD primer from 2 µM to 200 µM in all reactions; 3) reducing the total reaction volume from 20 µL to 10 µL; 4) extending the length of PCR extension cycle from 2.5 min to 4 min for all PCR programs; and 5) reducing the number of PCR programs from 3 to 2 with revised cycling conditions. Following this newly optimized procedure, a reduced number of synthetic oligonucleotide primers and PCR reaction cycles are required for the amplification of multiple target-specific PCR products with various fragment sizes of up to 3.5 kbp using total genomic DNA as template (FIG. 1).

Figure 3A:
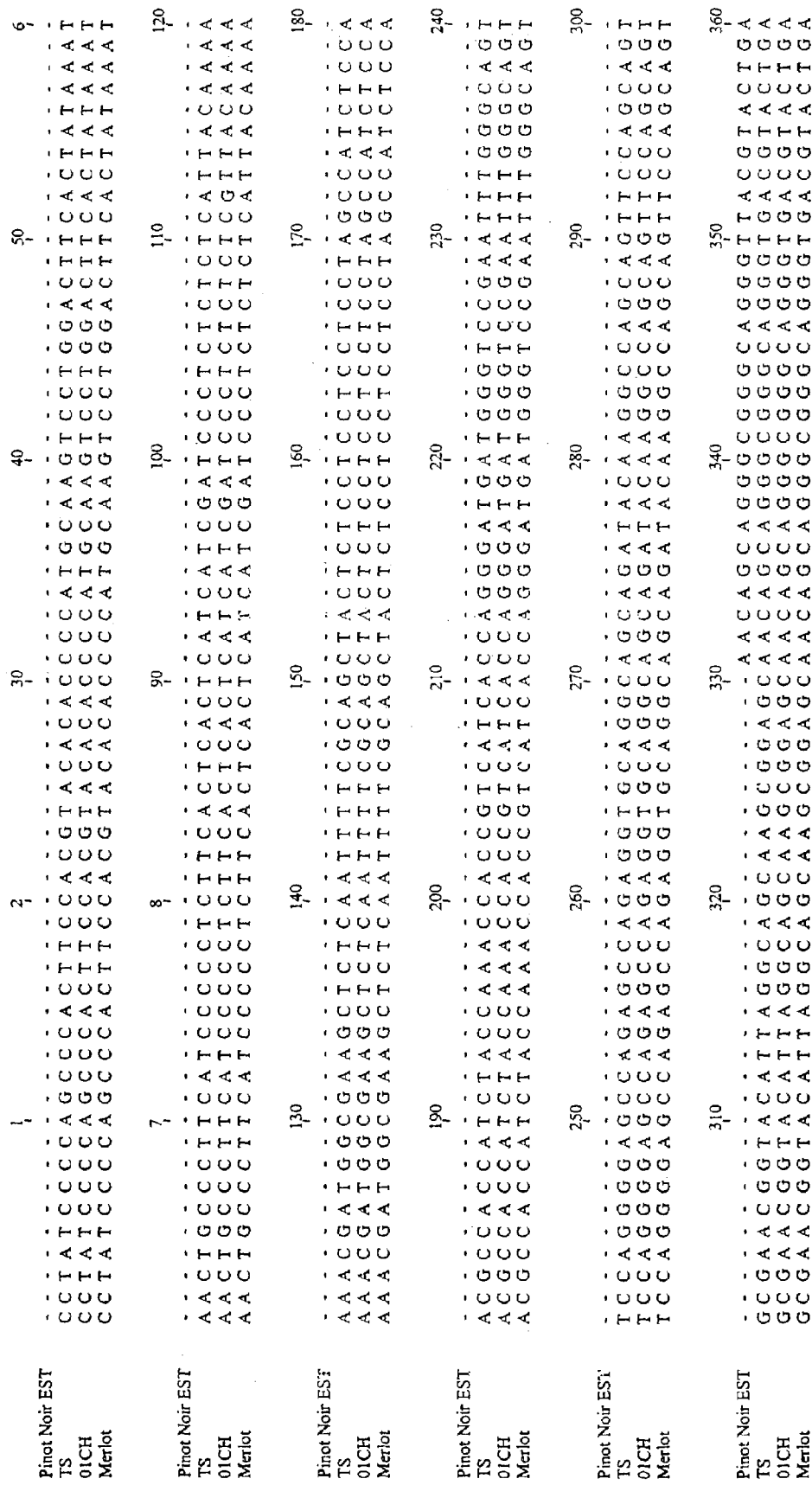
FIG. 3 shows an alignment of 2S albumin gene and promoter sequences from 4 different grape genotypes. TS=Thompson Seedless. 01CH=Chardonnay clone 1.
Figure 3B:
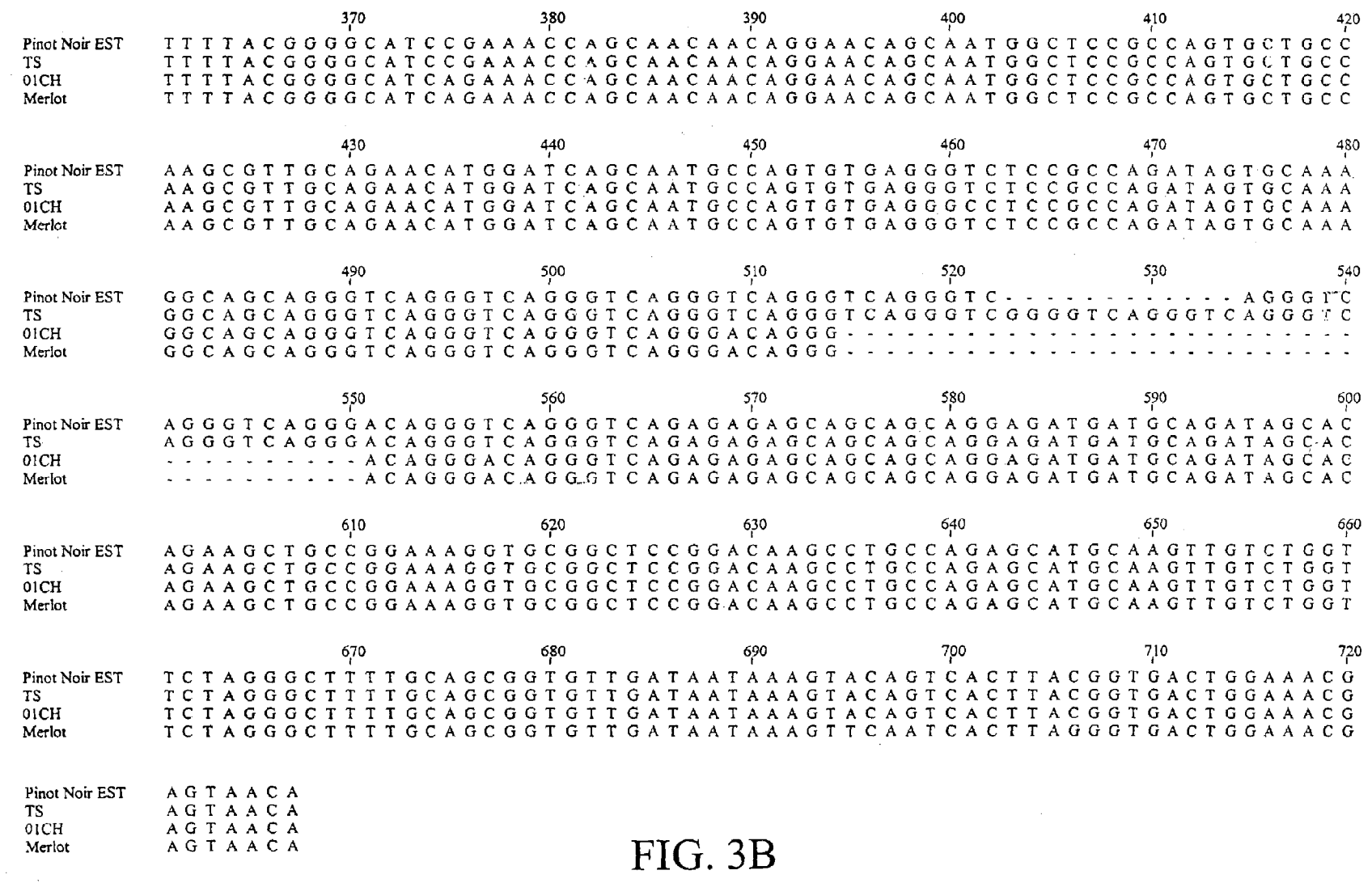

For the amplification of unknown DNA sequences flanking the partially sequenced 2S albumin-like gene in grape, PCR primers AB 1, AB2, and AB3 were designed from the published expressed sequence tag (EST) (Ageorges, 2000) that showed partial sequence homology to the seed-specific 2S albumin gene of other species. The use of TAIL-PCR with genomic DNA from a grape genotype (cv. Merlot) and the improved procedure resulted in several PCR products ranging from 0.4 to 2.8 kbp 5' upstream of the primer sites. These PCR products were cloned and subsequently sequenced. Based on nucleotide sequencing data, the complete coding sequence of the grape 2S albumin gene and the 5' upstream promoter region were identified (FIG. 2). DNA sequences were subsequently amplified from other grape genotypes, including Chardonnay and Thompson Seedless. Alignment of the 2S albumin gene sequences from different grape genotypes revealed striking variations, including a deletion of up to 24 bp of coding sequence within the coding region, while the majority of the gene promoter region showed a high sequence homology (FIG. 3).

2S Albumin Gene and 5' Upstream Sequences from Grape.

To determine the sequence identity of the PCR products obtained previously, both the 1.9 and 0.4 kbp DNA fragments (FIG. 1, indicated by arrows) were isolated from an agarose gel and cloned into pGEM-T vector for nucleotide sequencing. Subsequent sequence alignment revealed that the entire sequence of the 0.4 kbp DNA fragment was identical to the 3' end region of the 1.9 kbp fragment (data not shown). In addition, sequences homologous to the AB3 primer and the previously extended region of the EST clone were found at the 3' end region, while sequences similar to AD3 were present in the 5' end region of both DNA fragments (FIG. 2). Thus, these amplified fragments were the result of target-specific amplification from the genomic location containing the 2S albumin gene.

Analysis of amplified DNA sequences indicated that the 2S albumin gene from cv. Merlot was comprised of a single open reading frame of 504 nucleotides encoding a deduced amino acid sequence of 167 residues (FIG. 2). This deduced protein contained 49 glutamine (Q) residues—approximately 29% of the amino acid content. Examination of the deduced amino acid sequence confirmed the presence of a unique pattern of cysteine residue placement, C . . . C . . . / . . . CC . . . CXC . . . C . . . C . . . , that is well conserved among 2S albumins (Rico et al., 1996).

A TATA box was also identified in a region 63-nucleotides upstream from the ATG start codon (FIG. 2). The 2S albumin gene may have an estimated 5'-untranslated region (5' UTR) of about 25 nucleotides, similar to that commonly associated with 2S albumin genes of other species (Tai et al., 2001). In addition, several cis acting elements and DNA motifs associated with functional seed-specific promoters, such as cotyledon box (Conceicao and Krebbers 1994), F1, F2, and F3 elements (Vincentz et al., 1997), and G-box (Ezcurra et al., 2000), were present within a region upstream of the TATA box (FIG. 2).

To examine DNA sequence diversity of the 2S albumin gene, a forward primer GTU-51 (SEQ ID NO. 11) and a reverse primer TSA-33 (SEQ ID NO. 12) were used to amplify a 0.9 kbp region covering the entire 2S albumin gene and part of the 5' upstream sequence from cvs. Chardonnay clone 1 and Thompson Seedless. These two primers were synthesized based on the previously determined DNA sequences obtained from cv. Merlot.

Comparative sequence analysis of the 0.9 kb DNA fragment amplified from the different grape genotypes revealed significant variation within the ORF (FIG. 3). The 540 upstream region was identical in all genotypes examined, except for a single A to G substitution within the 5' UTR (at nucleotide -15 relative to the ATG start codon) from the amplified sequence of cv. Chardonnay clone 1. This high level of sequence homology indicated that the 0.9 kbp DNA fragment amplified from these different genotypes was derived from the same genomic location. Several sporadic incidences of single nucleotide substitutions were identified within the gene region contained within the EST in all genotypes. Among these substitutions, only one nucleotide change from deoxythymidine to deoxyguanosine (T to G) resulted in an amino acid change (from tyrosine (Y) in cv. Pinot Noir to arginine (R) in the other three genotypes), whereas other substitutions occurred at the wobble position of respective codons and did not result in a change in the amino acid sequence (FIG. 3). Sequence variations were found within a region encoding glutamine-glycine (Q-G) repeats near the 3' end of the gene. A 12 bp insertion was identified in cv. Thompson Seedless, while a deletion of 24 bp was evident in cvs. Chardonnay clone 1 and Merlot (FIG. 3), when compared to cv. Pinot Noir. These deletions changed the number of Q-G repeats but did not result in a frame-shift in the ORF (FIG. 3).

EXAMPLE 2

Confirmation of Promoter Functionality

Figure 4A:
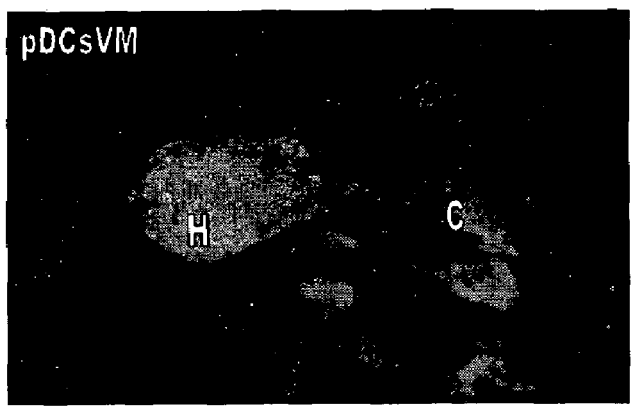
FIG. 4 shows a transient GFP expression in transformed SE of grape (*V. vinifera* cv. Thompson Seedless) directed by different promoters. Plasmid pDCsVM contains a double enhancer CsVMV promoter, plasmid pAL contains a grape 2S albumin gene promoter. Photographs were taken 6 days after *Agrobacterium*-mediated transformations. H=hypocotyl; C=cotyledon.
Figure 4B:
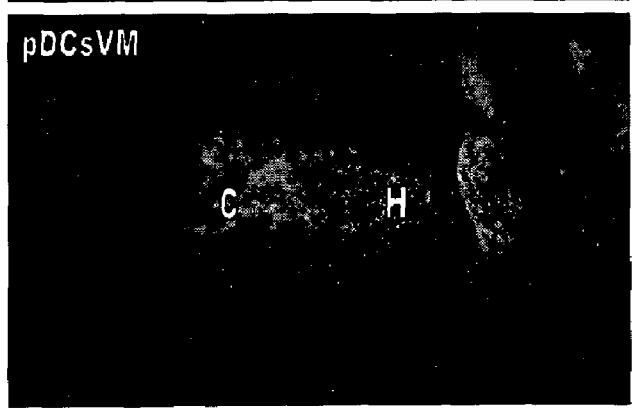
Figure 4C:
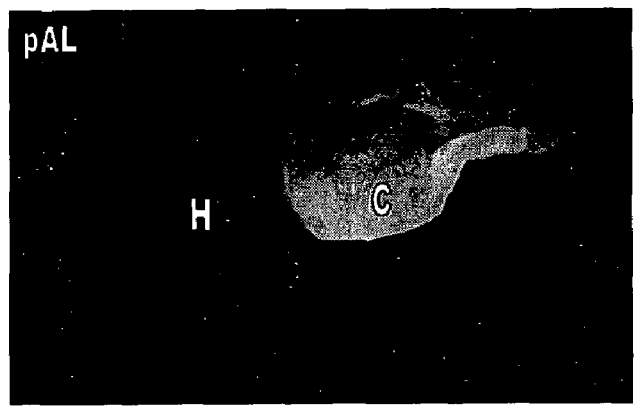
Figure 4D:
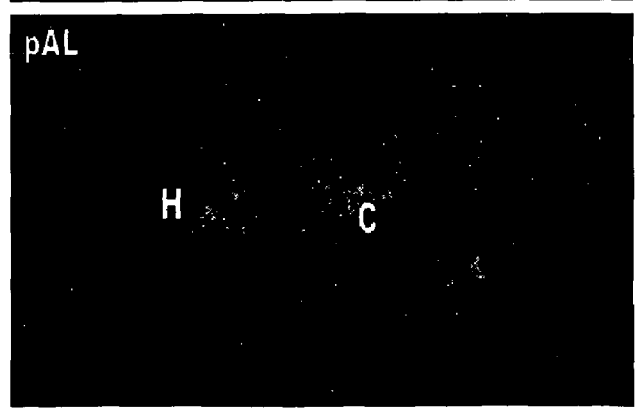

The expression activity of the grape 2S albumin gene promoter was confirmed by using transient GFP expression analysis in homologous host grape and in heterologous host tobacco. A 587 bp promoter sequence 5' upstream of the putative transcription start site of the 2S albumin gene was introduced into a transformation binary vector pAL and used to direct the expression of a bifunctional EGFP/NPTII fusion gene (Li et al., 2001). *Agrobacterium*-mediated transformation of grape SE using pAL resulted in high levels of GFP expression that were comparable to the level obtained by using a transformation vector pDCsVM containing a double enhancer CsVMV promoter (FIG. 4) (Li et al., 2001). No GFP-dependent fluorescence was detected in leaf cells of both grape and tobacco (data not shown). GFP expression controlled by the viral promoter (pDCsVM) was found in cells over the entire SE explant (FIGS. 4A and 4B) and in leaf disks of both grape and tobacco (data not shown). Noticeably, GFP expression in grape SE directed by the 2S albumin gene promoter (pAL) was mainly confined to the cotyledonary tissue but not hypocotyls tissue (FIGS. 4C and 4D). Accordingly, the 587 bp region of 2S albumin gene promoter tested herein is capable of conferring seed tissue specific transgene expression at a high level.

EXAMPLE 3

2S Albumin Protein and its Promoter

The storage protein 2S albumin constitutes a major component in seeds of many dicot species. For instance, 2S albumin accounts for up to 20% of the total protein content in mature seeds of rape, sunflower and Brazil nut. Due to its abundance and important role as a nutritional supply source, 2S albumin has been the subject of intensive studies of protein manipulation via genetic engineering. In addition, other unique functions such as antimycotic and antibacterial activities associated with glutamine-rich 2S albumins have attracted the attention of plant scientists (Barciszewski et al., 2000). The grape 2S albumin protein with variegated sequence features among different genotypes may serve as an excellent model for structural and functional studies of this type of important protein in this species.

In the past, a number of 2S albumin gene promoters have been isolated from a variety of plant species and characterized in great detail (Vincentz et al., 1997; Guerche et al., 1990). Several cis acting elements responsible for developmentally regulated transcription activation of 2S albumin genes from different plant species have been identified. These elements include cotyledon box (Conceicao and Krebbers, 1994), F1, F2, and F3 elements (Vincentz et al., 1997) and G-box (Ezcurra et al., 2000), etc. The majority of these known cis elements are also found within the exemplified 587 bp promoter fragment of the invention.

Tissue-specific promoters of the subject invention provides advantageous applications in genetic transformation of grape. A promoter of the invention can be used to drive transgene expression in seed tissues. In addition, it can provide controlled expression of selectable marker genes in certain tissues of explants used to recover transgenic plants during the transformation process, and the subsequent cessation of marker gene expression at the whole plant level, and in non-seed cell types.

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 6,395,964
U.S. Pat. No. 5,623,067
U.S. Pat. No. 5,589,615
U.S. Pat. No. 5,487,991

U.S. Pat. No. 5,380,831
U.S. Pat. No. 5,567,862
U.S. Pat. No. 5,567,600
U.S. Pat. No. 6,013,523
U.S. Pat. No. 6,015,891
U.S. Pat. No. 4,683,195
U.S. Pat. No. 4,683,202
U.S. Pat. No. 4,800,159
U.S. Pat. No. 6,080,914
U.S. Pat. No. 5,986,174

Ageorges, A. (2000) "EST0004 Grape berries Lamda Zap II Library Vitis vinifera cDNA clone A099 3' similar to albumin seed storage protein precursor from *Juglans regia* (U66866), mRNA sequence" GenBank Accession No. AW707958.

Altschul, S. F. et al. (1990) "Basic Local Alignment Search Tool" *J. Mol. Biol.* 215:403-410.

Altschul, S. F. et al. (1997) "Gapped BLAST and PSI-BLAST: A New Generation of Protein Database Search Programs" *Nucl. Acids Res.* 25:3389-3402.

An, Y. Q., McDowell, M. J., Huang, S., McKinney, E. C., Chambliss, S., Meagher, R. B. (1996) "Strong, constitutive expression of the *Arabidopsis* ACT2/ACT8 actin subclass in vegetative tissues" *Plant J.* 10:107-121.

Barciszewski, J., Szymanski, M., Haertle, T. (2000) "Minireview: analysis of rape seed napin structure and potential roles of the storage protein" *J. Protein Chem.* 19:249-254.

Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.

Boutilier, K., Hattori, J., Baum, B. R., Miki, B. L. (1999) "Evolution of 2S albumin seed storage protein genes in the *Brassicaceae*" *Biochem System Ecol* 27:223-234.

Burrow M. D., Chlan, C. A., Sen, P., Murai, N. (1990) "High frequency generation of transgenic tobacco plants after modified leaf disk cocultivation with *Agrobacterium tumefaciens*" Plant Mol Biol Rep 8:153-168.

Chatthai, M., Misra, S. (1998) "Sequence and expression of embryogenesis-specific cDNA encoding 2S seed storage proteins in *Pseudotsuga menziesii* (Mirb.) Franco" *Planta* 206:138-145.

Conceicao, A. S., Krebbers, E. (1994) "A cotyledon regulatory region is responsible for the different spatial expression patterns of *Arabidopsis* 2S albumin genes" Plant J 5:493-505.

Corneille, S., Lutz, K., Svab, Z., Maliga, P. (2001) "Efficient elimination of selectable marker genes from the plastid genome by the CRE-lox site-specific recombination system" *Plant J.* 27:171-178.

Dasgupta, S., Dasgupta, J., Mandal, R. K. (1993) "Cloning and sequencing of 5' flanking sequence from the gene encoding 2S storage protein, from two *Brassica* species" *Gene* 133:301-302.

De Lumen, B. O., Galvez, A. F., Revilleza, M. J., Krenz, D. C. (1999) "Molecular strategies to improve the nutritional quality of legume proteins" *Adv Exp Med Biol.* 464:117-126.

D'Halluin, K., De Block, M., Denecke, J., Janssens, J., Leemans, J., Reynaerts, A., Botterman, J. (1993) "The bar gene as selectable and screenable marker in plant engineering" *Methods Enzymol.* 216:415-426.

Dharmapuri, S., Rosati, C., Pallara, P., Aquilani, R., Bouvier, F., Camara, B., Giuliano, G. (2002) "Metabolic engineering of xanthophylls content in tomato fruits" *FEBS Lett.* 519:30-34.

Ezcurra, I., Wycliffe, P., Nehlin, L., Ellerstrom, M., Rask, L. (2000) "Transactivation of the *Brassica napus* napin promoter by AB 13 requires interaction of the conserved B2 and B3 domains of AB13 with different cis-elements: B2 mediates activation through an ABRE, whereas B3 interacts with an RY/G-box" *Plant J.* 24:57-66.

Fischer, R., Emans, N. (2000) "Molecular farming of pharmaceutical proteins" *Transgenic Res.* 9:279-299.

Galili, G., Hofgen, R. (2002) "Metabolic engineering of amino acids and storage proteins in plants" *Meta Eng* 4:3-11.

Ger, M. J., Chen, C. H., Hwang, S. Y., Huang, H. E., Podile, A. R., Dayakar, B. V., Feng, T. Y. (2002) "Constitutive expression of hrap gene in transgenic tobacco plant enhances resistance against virulent bacterial pathogens by induction of a hypersensitive response" *Mol Plant Microbe Interact* 15:764-773.

Gray, D. J. (1992) "Somatic embryogenesis and plant regeneration from immature zygotic embryos of muscadine grape (*Vitis rotundifolia*) cultivars" *Am. J. Bot.* 79:542-546.

Guerche, P., Tire, C., De Sa, F. G., De Clercq, A., Van Montagu, M., Krebbers, E. (1990) "Differential Expression of the *Arabidopsis* 2S Albumin Genes and the Effect of increasing Gene Family Size" *Plant Cell.* 2:469-478.

Hood, E. E., Jilka, J. M. (1999) "Plant-based production of xenogenic proteins" *Curr Opin Biotechnol.* 10:382-386.

Iamtham, S., Day, A. (2000) "Removal of antibiotic resistance genes from transgenic tobacco plastids" *Nat Biotechnol.* 18:1172-1176.

Jaeger, G. D., Scheffer, S., Jacobs, A., Zambre, M., Zobell, O., Goossens, A., Depicker, A., Angenon, G. (2002) "Boosting heterologous protein production in transgenic dicotyledonous seeds using *Phaseolus vulgaris* regulatory sequences" *Nat Biotech* 20:1265-1268.

Karlin S., Altschul, S. F. (1990) "Methods for Assessing the Statistical Significance of Molecular Sequence Features by Using General Scoring Schemes" *Proc. Natl. Acad. Sci. USA* 87:2264-2268.

Karlin S., Altschul, S. F. (1993) "Applications and Statistics for Multiple High-Scoring Segments in Molecular Sequences" *Proc. Natl. Acad. Sci. USA* 90:5873-5877.

Kloti, A., He, X., Potrykus, I., Hohn, T., Futterer, J. (2002) "Tissue-specific silencing of a transgene in rice" Proc Natl Acad Sci USA. 99:10881-10886.

Koo, J. C., Chun, H. J., Park, H. C., Kim, M. C., Koo, Y. D., Koo, S. C., Ok, H. M., Park, S. J., Lee, S. H., Yun, D. Y., Lim, C. O., Bahk, J. D., Lee, S. Y., Cho, M. J. (2002) "Over-expression of a seed specific hevein-like antimicrobial peptide from Pharbitis nil enhances resistance to a fungal pathogen in transgenic tobacco plants" *Plant Mol Biol* 50:441-452.

Li, Z., Jayasankar, S., Gray, D. J. (2002) "Use of marker genes to target disease resistance gene expression in grape" 10th IAPTC&B Congress, *Plant Biotechnology 2002 and Beyond*, Jun. 23-29, 2002, page 58-A.

Li, Z., Jayasankar, S., Gray, D. J. (2001) "Expression of a bifunctional green fluorescent protein (GFP) fusion marker under the control of three constitutive promoters and enhanced derivatives in transgenic grape (*Vitis vinifera*)" *Plant Sci.* 160:877-887.

Liu, Y. G., Whittier, R. F. (1995) "Thermal asymmetric interlaced PCR: automatable amplification and sequencing of insert end fragments from P1 and YAC clones for chromosome walking" *Genomics* 25:674-681.

Liu, Y. G., Huang, N. (1998) "Efficient amplification of insert end sequences from bacterial artificial chromosome clones by thermal asymmetric interlaced PCR" *Plant Mol. Biol. Rep.* 16:175-181.

Lodhi, M. A., Yes, G. N., Weeden, N. F., Reisch, B. J. (1994) "A simple and efficient method for DNA extraction from grapevine cultivars and Vitis species" *Plant Mol. Biol. Rep.* 12:6-13.

Longstaff, M., Brigneti, G., Boccard, F., Chapman, S., Baulaube, D. (1993) "Extreme resistance to potato virus X infection in plants expressing a modified component of the putative viral replicase" *EMBO J.* 12:379-386.

Maniatis, T., Fritsch, E. F., Sambrook, J. (1982) *Molecular Cloning: A Laboratory Manual*, Cold Spring Harbor Laboratory, Cold Spring Harbor, N.Y.

Maniatis, T., Fritsch, E. F., Sambrook, J. (1989) Molecular Cloning: *A Laboratory Manual*, 2d Edition, Cold Spring Harbor Laboratory, Cold Spring Harbor, N.Y.

Molvig, L., Tabe, L. M., Eggum, B. O., Moore, A. E., Craig, S., Spencer, D., Higgins, T. J. (1997) "Enhanced methionine levels and increased nutritive value of seed of transgenic lupins (*Lupinus angustifolius* L.) expressing a sunflower seed albumin gene" *Proc Natl Acad Sci USA* 94:8393-8398.

Muntz, K. (1998) "Deposition of storage proteins" *Plant Mol Biol* 38:77-99.

Muntz, K., Christov, V., Saalbach, G., Saalbach, I., Waddell, D., Pickardt, T., Schieder, O, Wustenhagen, T. (1998) "Genetic engineering for high methionine grain legumes" *Nahrung* 42:125-127.

*Nucleic Acid Hybridization: A Practical Approach* (1995) Hames, B. D., S. J. Higgins, eds., IRL Press.

Perlak, F. J., Deaton, R. W., Armstrong, T. A., Fuchs, R. L., Sims, S. R., Greenplate, J. T., Fischhoff, D. A. (1990) "Insect resistant cotton plants" *Biotechnology* (N.Y.) 8:939-943.

Raynal, M., Depigny, D., Grellet, F., Delseny, M. (1991) "Characterization and evolution of napin-encoding genes in radish and related crucifers" *Gene* 99:77-86.

Riico M., Bruix, M., Gonzalez, C., Monsalve, R. I., Rodriguez, R. (1996)"¹H NMR assignment and global fold of napin BnIb, a representative 2S albumin seed protein" *Biochem* 35:15672-15682.

Roeckel, P., Oancia, T., Drevet, J. (1997) "Effects of seed-specific expression of a cytokinin biosynthetic gene on canola and tobacco phenotypes" *Transgenic Res* 6:133-141.

Scarafoni, A., Carzaniga, R., Harris, N., Croy, R. R. (2001) "Manipulation of the napin primary structure alters its packaging and deposition in transgenic tobacco (*Nicotiana tabacum* L.) seeds" *Plant Mol Biol* 46:727-739.

Shewry P. R., Napier, J. A., Tatham, A. S. (1995) "Seed storage proteins: structures and biosynthesis" *Plant Cell* 7:945-956.

Stalberg, K., Elierstrom, M., Josefsson, L. G., Rask, L. (1993) "Deletion analysis of a 2S seed storage protein promoter of *Brassica napus* in transgenic tobacco" *Plant Mol Biol* 23:671-683.

Tai, S. S. K., Lee, T. T. T., Tsai, C. C. Y., Yiu, T. J., Tzen, J. T. C. (2001) "Expression pattern and deposition of three storage proteins 11S globulin, 2S albumin and 7S globulin in maturing sesame seeds" *Plant Physiol Biochem* 39:981-992.

Terauchi R, Kahl, G. (2000) "Rapid isolation of promoter sequences by TAIL-PCR: the 5'-flanking regions of Pal and Pgi genes from yams (*Dioscorea*)" *Mol Gen Genet* 263:554-60.

Terras, F. R. G., Torrekens, S., Van Leuven, F., Osbron, R. W., Vanderleyden, J., Cammue, B. P. A., Broekaert, W. F. (1993) "A new family of basic cysteine-rich plant antifungal proteins from *Brassicaceae* species" *FEBS Lett* 316:233-240.

Teuber, S. S., Dandekar, A. M., Peterson, W. R., Sellers, C. L. (1998) "Cloning and sequencing of a gene encoding a 2S albumin seed storage protein precursor from English walnut (*Juglans regia*), a major food allergen" *J. Allergy Clin Immunol* 101:807-814.

Vincentz, M., Leite, A., Neshich, G., Vriend, G., Mattar, C., Barros, L., Weinberg, D., de Almeida, E. R., de Carvalho, M. P., Aragao, F., Gander, E. S. (1997) "ACGT and vicilin core sequences in a promoter domain required for seed-specific expression of a 2S storage protein gene are recognized by the opaque-2 regulatory protein" *Plant Mol Biol.* 34:879-889.

Wei, C. F. et al. (1983) "Isolation and Comparison of Two Molecular Species of the BAL 31 Nuclease from *Alteromonas espejiana* with Distinct Kinetic Properties" *J. Biol. Chem.* 258(22):13506-13512.

Yang, T. T. et al. (1996) "Optimized Codon Usage and Chromophore Mutations Provide Enhanced Sensitivity with the Green Fluorescent Protein" *Nucleic Acid Research* 24(22):4592-4593.

Zheng, Z., Kawagoe, Y., Xiao, S., Li, Z., Okita, T., Hau, T. L., Lin, A., Murai, N. (1993) "5' Distal and Proximal Cis-acting Regulator Elements are Required for Developmental Control of a Rice Seed Storage Protein Glutelin Gene" *Plant J.* 4:357-366.

Zuo, J., Niu, Q. W., Moller, S. G., Chua, N. H. (2001) "Chemical-regulated, site-specific DNA excision in transgenic plants" *Nat Biotechnol.* 19:157-161.

We claim:

1. An isolated polynucleotide comprising a promoter sequence that exhibits functional promoter activity, wherein said polynucleotide comprises the nucleotide sequence shown in SEQ ID NO:1 or SEQ ID NO: 2.

2. An expression construct comprising a polynucleotide comprising at least one promoter sequence that exhibits functional promoter activity, wherein said polynucleotide comprises the nucleotide sequence shown in SEQ ID NO:1 or SEQ ID NO: 2.

3. The expression construct according to claim 2, wherein said construct comprises multiple copies of said promoter sequence.

4. The expression construct according to claim 2, wherein said construct comprises a nucleotide sequence encoding a protein operably linked to said promoter sequence.

5. The expression construct according to claim 4, wherein said protein is a plant protein.

6. The expression construct according to claim 4, wherein said protein is a non-plant protein.

7. The expression construct according to claim 2, wherein said construct comprises a selectable marker gene.

8. The expression construct according to claim 7, wherein said selectable marker gene encodes antibiotic resistance.

9. The expression construct according to claim 8, wherein said antibiotic resistance is to an antibiotic selected from the group consisting of hygromycin, kanamycin, bleomycin, G418, streptomycin, paromomycin, neomycin, and spectinomycin.

10. The expression construct according to claim 7, wherein said selectable marker gene encodes herbicide resistance.

11. The expression construct according to claim 10, wherein said herbicide resistance is phosphinothricin acetyl transferase or glyphosate.

12. The expression construct according to claim 7, wherein said selectable marker gene encodes a protein selected from the group consisting of β-glucuronidase, luciferase, and green fluorescence protein.

13. The expression construct according to claim 2, wherein said construct comprises a transcription termination sequence.

14. The expression construct according to claim 2, wherein said construct comprises a translation termination sequence.

15. The expression construct according to claim 2, wherein said construct comprises one or more enhancer elements.

16. The expression construct according to claim 2, wherein said construct comprises a nucleotide sequence that directs polyadenylation of a transcribed polynucleotide.

17. The expression construct according to claim 2, wherein said construct comprises a transposon sequence.

18. A cell transformed with a polynucleotide comprising a promoter sequence that exhibits functional promoter activity, wherein said polynucleotide comprises the nucleotide sequence shown in SEQ ID NO:1 or SEQ ID NO: 2.

19. The cell according to claim 18, wherein said cell is a plant cell.

20. A plant or plant tissue grown from plant cell of claim 19.

21. A transformed or transgenic plant, or the transgenic progeny thereof, comprising an isolated polynucleotide that comprises a promoter sequence, wherein said polynucleotide comprises the nucleotide sequence shown in SEQ ID NO. 1 or SEQ ID NO. 2.

22. The plant according to claim 21, wherein said plant is a monocot.

23. The plant according to claim 22, wherein said monocot plant is selected from the group consisting of rice, wheat, barley, oats, sorghum, maize, sugarcane, pineapple, onion, bananas, coconut, lilies, grasses, and millet.

24. The plant according to claim 21, wherein said plant is a dicot.

25. The plant according to claim 24, wherein said dicot plant is selected from the group consisting of peas, alfalfa, tomato, melon, chickpea, chicory, clover, kale, lentil, soybean, tobacco, potato, sweet potato, radish, cabbage, rape, apple trees, grape, cotton, sunflower, thale cress, and lettuce.

26. The expression construct according to claim 15, wherein said one or more enhancer elements are 35S enhancer elements.

27. The cell according to claim 18, wherein said plant cell is a grape cell.

28. A transformed or transgenic plant, of the transgenic progeny thereof, comprising an isolated polynucleotide that comprises a promoter sequence, wherein said polynucleotide comprises the nucleotide sequence shown in SEQ ID NO: 1 or SEQ ID NO: 2.

* * * * *

UNITED STATES PATENT AND TRADEMARK OFFICE
CERTIFICATE OF CORRECTION

PATENT NO. : 7,250,296 B2
APPLICATION NO. : 10/382066
DATED : July 31, 2007
INVENTOR(S) : Zhijian T. Li and Dennis J. Gray It is certified that error appears in the above-identified patent and that said Letters Patent is hereby corrected as shown below:

Column 5,
Line 21 "modem molecular" should read --modern molecular--.

Column 10,
Line 50 "in 0.80% agarose" should read --in 0.8% agarose--.

Column 12,
Line 35 "AB 1, AB2, and AB3" should read --AB1, AB2, and AB3--.

Column 13,
Lines 32 and 33 "The 540 upstream" should read --The 5' upstream--.

Column 16,
Line 7 "by AB 13" should read --by AB13--.

Column 38,
Claim 27: "The cell according to claim 18, wherein said plant cell is a grape cell." should read --The cell according to claim 19, wherein said plant cell is a grape cell.--.

Column 38,
Claim 28: "A transformed or transgenic plant, of the transgenic progeny thereof, comprising an isolated polynucleotide that comprises a promoter sequence, wherein said polynucleotide comprises the nucleotide sequence shown in SEQ ID NO: 1 or SEQ ID NO: 2." should read --The plant or plant tissue according to claim 20, wherein said plant or plant tissue is grape plant.--.

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,250,296 B2 Page 1 of 1
APPLICATION NO. : 10/382066
DATED : July 31, 2007
INVENTOR(S) : Zhijian T. Li and Dennis J. Gray It is certified that error appears in the above-identified patent and that said Letters Patent is hereby corrected as shown below:

Column 5,
Line 21 "modem molecular" should read --modern molecular--.

Column 10,
Line 50 "in 0.80% agarose" should read --in 0.8% agarose--.

Column 12,
Line 35 "AB 1, AB2, and AB3" should read --AB1, AB2, and AB3--.

Column 13,
Lines 32 and 33 "The 540 upstream" should read --The 5' upstream--.

Column 16,
Line 7 "by AB 13" should read --by AB13--.

Column 38, lines 25 and 26
Claim 27: "The cell according to claim 18, wherein said plant cell is a grape cell." should read --The cell according to claim 19, wherein said plant cell is a grape cell.--.

Column 38, lines 27-31
Claim 28: "A transformed or transgenic plant, of the transgenic progeny thereof, comprising an isolated polynucleotide that comprises a promoter sequence, wherein said polynucleotide comprises the nucleotide sequence shown in SEQ ID NO: 1 or SEQ ID NO: 2." should read --The plant or plant tissue according to claim 20, wherein said plant or plant tissue is grape plant.--.

This certificate supersedes the Certificate of Correction issued June 10, 2008.

Signed and Sealed this

Fifteenth Day of July, 2008

JON W. DUDAS
*Director of the United States Patent and Trademark Office*

SEQUENCE LISTING

<160> NUMBER OF SEQ ID NOS: 29

<210> SEQ ID NO 1
<211> LENGTH: 1164
<212> TYPE: DNA
<213> ORGANISM: Vitis vinifera cv. Merlot

<400> SEQUENCE: 1

```
cggaggctta atccagttga agagtgaagg ttgggccgga gccttacagc ccaaattgag    60
```

-continued

```
ttggtgggtt ggtgctgaga ggcttgtgtt caaagtccat atccattcga aaaaattttg    120
ccctcttgta taagcctcag gaatctcttt agcctttaat taaacctaaa tcctaccaaa    180
actgcccttc aaaattattg ctttgtttta ggtccaagaa tcctaaataa ggtctatttt    240
gaaacattcc taatggggtg gctttgctt ctccaaacag aagcatacta cttgctgttg     300
atgagcatgt ctgtcacctc caaaaaaagg acaaggtaac tttaactgca gcattaaatg    360
tataggaagc agtattacaa tcaaaatcag tttatggcag cctttccatg aatgctccca    420
tttcagcatg caaactaacc tccacacgtc cacacctccc accataaacc tgccctatcc    480
ccagcccact tccacgtaca caccccatgc aagtcctgga cttcactata ataactgcc    540 cttcatcccc ctcttcactc actcatcatc gatccctctc tctcattaca aaaaacgat    600 ggcgaagctc tcaattttcg cagctactct cctcctcctc ctagccatct ccaacgccac    660
catctaccaa accaccgtca tcaccaggga tgatgggtcc gaatttgggc agttccaggg    720
gagccagagc cagaggtgca ggcagcagat acaaggccag cagttccagc agtgcgaacg    780
gtacattagg cagcaagcgg agcaacagca gggcgggcag ggtgacgtac tgattttacg    840
gggcatcaga aaccagcaac aacaggaaca gcaatggctc cgccagtgct gccaagcgtt    900
gcagaacatg gatcagcaat gccagtgtga gggtctccgc cagatagtgc aaaggcagca    960
gggtcagggt cagggtcagg gacagggaca gggacaggct cagagagagc agcagcagga   1020
gatgatgcag atagcacaga agctgccgga aggtgcggc tccggacaag cctgccagag     1080
catgcaagtt gtctggttct agggcttttg cagcggtgtt gataataaag ttcaatcact   1140
tagggtgact ggaaacgagt aaca                                          1164

<210> SEQ ID NO 2
<211> LENGTH: 587
<212> TYPE: DNA
<213> ORGANISM: Vitis vinifera cv. Merlot

<400> SEQUENCE: 2
gcttaatcca gttgaagagt gaaggttggg ccggagcctt acagcccaaa ttgagttggt     60
gggttggtgc tgagaggctt gtgttcaaag tccatatcca ttcgaaaaaa ttttgccctc    120
ttgtataagc ctcaggaatc tctttagcct ttaattaaac ctaaatccta ccaaaactgc    180
ccttcaaaat tattgctttg ttttaggtcc aagaatccta ataaggtct attttgaaac     240 attcctaatg gggtgggctt tgcttctcca aacagaagca tactacttgc tgttgatgag    300
catgtctgtc acctccaaaa aaggacaag gtaactttaa ctgcagcatt aaatgtatag    360
gaagcagtat tacaatcaaa atcagtttat ggcagccttt ccatgaatgc tcccatttca    420
gcatgcaaac taacctccac acgtccacac tcccaccat aaacctgccc tatccccagc    480
ccacttccac gtacacaccc catgcaagtc ctggacttca ctataaataa ctgcccttca    540 tcccctctt cactcactca tcatcgatcc ctctctctca ttacaaa                  587

<210> SEQ ID NO 3
<211> LENGTH: 721
<212> TYPE: DNA
<213> ORGANISM: Vitis vinifera cv. Thompson Seedless

<400> SEQUENCE: 3
cctatcccca gcccacttcc acgtacacac cccatgcaag tcctggactt cactataaat     60
aactgccctt catcccctc ttcactcact catcatcgat ccctctctct cattacaaaa    120
aaacgatggc gaagctctca attttcgcag ctactctcct cctcctccta gccatctcca    180
```

```
acgccaccat ctaccaaacc accgtcatca ccagggatga tgggtccgaa tttgggcagt    240
tccaggggag ccagagccag aggtgcaggc agcagataca aggccagcag ttccagcagt    300
gcgaacggta cattaggcag caagcggagc aacagcaggg cgggcagggt gacgtactga    360
ttttacgggg catccgaaac cagcaacaac aggaacagca atggctccgc cagtgctgcc    420
aagcgttgca gaacatggat cagcaatgcc agtgtgaggg tctccgccag atagtgcaaa    480
ggcagcaggg tcagggtcag ggtcagggtc agggtcaggg tcgggtcag ggtcagggtc     540 agggacaggg tcagggtcag agagagcagc agcaggagat gatgcagata gcacagaagc    600
tgccggaaag gtgcggctcc ggacaagcct gccagagcat gcaagttgtc tggttctagg    660
gcttttgcag cggtgttgat aataaagtac agtcacttac ggtgactgga aacgagtaac    720
a                                                                    721
```

<210> SEQ ID NO 4
<211> LENGTH: 691
<212> TYPE: DNA
<213> ORGANISM: Vitis vinifera cv. Thompson Seedless

<400> SEQUENCE: 4

```
cctatcccca gcccacttcc acgtacacac cccatgcaag tcctggactt cactataaat    60
aactgccctt catccccctc ttcactcact catcatcgat ccctctctct cgttacaaaa    120
aaacgatggc gaagctctca attttcgcag ctactctcct cctcctccta gccatctcca    180
acgccaccat ctaccaaacc accgtcatca ccagggatga tgggtccgaa tttgggcagt    240
tccaggggag ccagagccag aggtgcaggc agcagataca aggccagcag ttccagcagt    300
gcgaacggta cattaggcag caagcggagc aacagcaggg cgggcagggt gacgtactga    360
ttttacgggg catcagaaac cagcaacaac aggaacagca atggctccgc cagtgctgcc    420
aagcgttgca gaacatggat cagcaatgcc agtgtgaggg cctccgccag atagtgcaaa    480
ggcagcaggg tcagggtcag ggtcagggac agggacaggg acagggtcag agagagcagc    540
agcaggagat gatgcagata gcacagaagc tgccggaaag gtgcggctcc ggacaagcct    600
gccagagcat gcaagttgtc tggttctagg gcttttgcag cggtgttgat aataaagtac    660
agtcacttac ggtgactgga aacgagtaac a                                   691
```

<210> SEQ ID NO 5
<211> LENGTH: 28
<212> TYPE: DNA
<213> ORGANISM: Artificial Sequence
<220> FEATURE:
<223> OTHER INFORMATION: Primer sequence

<400> SEQUENCE: 5

```
ttcctgttgt tgctgctggt ttcggatg                                       28
```

<210> SEQ ID NO 6
<211> LENGTH: 22
<212> TYPE: DNA
<213> ORGANISM: Artificial Sequence
<220> FEATURE:
<223> OTHER INFORMATION: Primer sequence

<400> SEQUENCE: 6

```
atcagtacgt aaccctgccc gc                                             22
```

<210> SEQ ID NO 7

```
<211> LENGTH: 20
<212> TYPE: DNA
<213> ORGANISM: Artificial Sequence
<220> FEATURE:
<223> OTHER INFORMATION: Primer sequence

<400> SEQUENCE: 7
taatgagaga gagggatcga                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer sequence

<400> SEQUENCE: 8
ggatgaaggg cagttattta                                                 20

<210> SEQ ID NO 9
<211> LENGTH: 22
<212> TYPE: DNA
<213> ORGANISM: Artificial Sequence
<220> FEATURE:
<223> OTHER INFORMATION: Primer sequence

<400> SEQUENCE: 9
gcatggggtg tgtacgtgga ag                                              22

<210> SEQ ID NO 10
<211> LENGTH: 16
<212> TYPE: DNA
<213> ORGANISM: Artificial Sequence
<220> FEATURE:
<223> OTHER INFORMATION: Primer sequence
<220> FEATURE:
<221> NAME/KEY: MISC_FEATURE
<222> LOCATION: (1)..(1)
<223> OTHER INFORMATION: w represents a or t
<220> FEATURE:
<221> NAME/KEY: MISC_FEATURE
<222> LOCATION: (5)..(5)
<223> OTHER INFORMATION: n stands for a, t, g, or c
<220> FEATURE:
<221> NAME/KEY: MISC_FEATURE
<222> LOCATION: (8)..(8)
<223> OTHER INFORMATION: w represents a or t
<220> FEATURE:
<221> NAME/KEY: MISC_FEATURE
<222> LOCATION: (10)..(10)
<223> OTHER INFORMATION: n stands for a, t, g, or c
<220> FEATURE:
<221> NAME/KEY: MISC_FEATURE
<222> LOCATION: (13)..(13)
<223> OTHER INFORMATION: n stands for a, t, g, or c

<400> SEQUENCE: 10
wgtgnagwan canaga                                                     16

<210> SEQ ID NO 11
<211> LENGTH: 22
<212> TYPE: DNA
<213> ORGANISM: Artificial Sequence
<220> FEATURE:
<223> OTHER INFORMATION: Primer sequence

<400> SEQUENCE: 11
cctatcccca gcccacttcc ac                                              22
```

<210> SEQ ID NO 12
<211> LENGTH: 20
<212> TYPE: DNA
<213> ORGANISM: Artificial Sequence
<220> FEATURE:
<223> OTHER INFORMATION: Primer sequence

<400> SEQUENCE: 12

```
tgttactcgt ttccagtcac                                                  20
```

<210> SEQ ID NO 13
<211> LENGTH: 562
<212> TYPE: DNA
<213> ORGANISM: Vitis vinifera cv. Merlot

<400> SEQUENCE: 13

```
ttgggccgga gccttacagc ccaaattgag ttggtgggtt ggtgctgaga ggcttgtgtt       60
caaagtccat atccattcga aaaattttg ccctcttgta taagcctcag gaatctcttt      120
agcctttaat taaacctaaa tcctaccaaa actgcccttc aaaattattg ctttgtttta     180
ggtccaagaa tcctaaataa ggtctatttt gaaacattcc taatggggtg gctttgctt     240
ctccaaacag aagcatacta cttgctgttg atgagcatgt ctgtcacctc caaaaaaagg     300
acaaggtaac tttaactgca gcattaaatg tataggaagc agtattacaa tcaaaatcag     360
tttatggcag cctttccatg aatgctccca tttcagcatg caaactaacc tccacacgtc     420
cacacctccc accataaacc tgccctatcc ccagcccact tccacgtaca cacccccatgc    480
aagtcctgga cttcactata ataactgcc cttcatcccc ctcttcactc actcatcatc     540
gatccctctc tctcattaca aa                                             562
```

<210> SEQ ID NO 14
<211> LENGTH: 537
<212> TYPE: DNA
<213> ORGANISM: Vitis vinifera cv. Merlot

<400> SEQUENCE: 14

```
ttgagttggt ggggttggtgc tgagaggctt gtgttcaaag tccatatcca ttcgaaaaaa     60
ttttgccctc ttgtataagc ctcaggaatc tctttagcct ttaattaaac ctaaatccta    120
ccaaaactgc ccttcaaaat tattgctttg ttttaggtcc aagaatccta aataaggtct    180
attttgaaac attcctaatg gggtgggctt tgcttctcca aacagaagca tactacttgc    240
tgttgatgag catgtctgtc acctccaaaa aaaggacaag gtaactttaa ctgcagcatt    300
aaatgtatag gaagcagtat tacaatcaaa atcagtttat ggcagccttt ccatgaatgc    360
tcccatttca gcatgcaaac taacctccac acgtccacac ctcccaccat aaacctgccc    420
tatccccagc ccacttccac gtacacaccc catgcaagtc ctggacttca ctataaataa    480
ctgcccttca tcccctctt cactcactca tcatcgatcc ctctctctca ttacaaa       537
```

<210> SEQ ID NO 15
<211> LENGTH: 512
<212> TYPE: DNA
<213> ORGANISM: Vitis vinifera cv. Merlot

<400> SEQUENCE: 15

```
ggcttgtgtt caaagtccat atccattcga aaaattttg ccctcttgta taagcctcag      60
gaatctcttt agcctttaat taaacctaaa tcctaccaaa actgcccttc aaaattattg    120
ctttgtttta ggtccaagaa tcctaaataa ggtctatttt gaaacattcc taatggggtg    180
```

| | |
|---|---|
| ggctttgctt ctccaaacag aagcatacta cttgctgttg atgagcatgt ctgtcacctc | 240 |
| caaaaaaagg acaaggtaac tttaactgca gcattaaatg tataggaagc agtattacaa | 300 |
| tcaaaatcag tttatggcag cctttccatg aatgctccca tttcagcatg caaactaacc | 360 |
| tccacacgtc cacacctccc accataaacc tgccctatcc ccagcccact tccacgtaca | 420 |
| caccccatgc aagtcctgga cttcactata ataactgcc cttcatcccc ctcttcactc | 480 |
| actcatcatc gatccctctc tctcattaca aa | 512 |

<210> SEQ ID NO 16
<211> LENGTH: 487
<212> TYPE: DNA
<213> ORGANISM: Vitis vinifera cv. Merlot

<400> SEQUENCE: 16

| | |
|---|---|
| ttcgaaaaaa ttttgccctc ttgtataagc ctcaggaatc tctttagcct ttaattaaac | 60 |
| ctaaatccta ccaaaactgc ccttcaaaat tattgctttg ttttaggtcc aagaatccta | 120 |
| aataaggtct attttgaaac attcctaatg gggtgggctt tgcttctcca acagaagca | 180 |
| tactacttgc tgttgatgag catgtctgtc acctccaaaa aaaggacaag gtaactttaa | 240 |
| ctgcagcatt aaatgtatag gaagcagtat tacaatcaaa atcagtttat ggcagccttt | 300 |
| ccatgaatgc tcccatttca gcatgcaaac taacctccac acgtccacac ctcccaccat | 360 |
| aaacctgccc tatccccagc ccacttccac gtacacaccc catgcaagtc ctggacttca | 420 |
| ctataaataa ctgcccttca tcccctctct cactcactca tcatcgatcc ctctctctca | 480 |
| ttacaaa | 487 |

<210> SEQ ID NO 17
<211> LENGTH: 437
<212> TYPE: DNA
<213> ORGANISM: Vitis vinifera cv. Merlot

<400> SEQUENCE: 17

| | |
|---|---|
| ttaattaaac ctaaatccta ccaaaactgc ccttcaaaat tattgctttg ttttaggtcc | 60 |
| aagaatccta aataaggtct attttgaaac attcctaatg gggtgggctt tgcttctcca | 120 |
| aacagaagca tactacttgc tgttgatgag catgtctgtc acctccaaaa aaaggacaag | 180 |
| gtaactttaa ctgcagcatt aaatgtatag gaagcagtat tacaatcaaa atcagtttat | 240 |
| ggcagccttt ccatgaatgc tcccatttca gcatgcaaac taacctccac acgtccacac | 300 |
| ctcccaccat aaacctgccc tatccccagc ccacttccac gtacacaccc catgcaagtc | 360 |
| ctggacttca ctataaataa ctgcccttca tcccctctct cactcactca tcatcgatcc | 420 |
| ctctctctca ttacaaa | 437 |

<210> SEQ ID NO 18
<211> LENGTH: 387
<212> TYPE: DNA
<213> ORGANISM: Vitis vinifera cv. Merlot

<400> SEQUENCE: 18

| | |
|---|---|
| ttttaggtcc aagaatccta aataaggtct attttgaaac attcctaatg gggtgggctt | 60 |
| tgcttctcca aacagaagca tactacttgc tgttgatgag catgtctgtc acctccaaaa | 120 |
| aaaggacaag gtaactttaa ctgcagcatt aaatgtatag gaagcagtat tacaatcaaa | 180 |
| atcagtttat ggcagccttt ccatgaatgc tcccatttca gcatgcaaac taacctccac | 240 |
| acgtccacac ctcccaccat aaacctgccc tatccccagc ccacttccac gtacacaccc | 300 |

```
catgcaagtc ctggacttca ctataaataa ctgcccttca tccccctctt cactcactca      360
tcatcgatcc ctctctctca ttacaaa                                          387
```

<210> SEQ ID NO 19
<211> LENGTH: 562
<212> TYPE: DNA
<213> ORGANISM: Vitis vinifera cv. Merlot

<400> SEQUENCE: 19

```
gcttaatcca gttgaagagt gaaggttggg ccggagcctt acagcccaaa ttgagttggt       60
gggttggtgc tgagaggctt gtgttcaaag tccatatcca ttcgaaaaaa ttttgccctc      120
ttgtataagc ctcaggaatc tctttagcct ttaattaaac ctaaatccta ccaaaactgc      180
ccttcaaaat tattgctttg ttttaggtcc aagaatccta ataaggtct attttgaaac      240 attcctaatg gggtgggctt tgcttctcca aacagaagca tactacttgc tgttgatgag      300
catgtctgtc acctccaaaa aaaggacaag gtaactttaa ctgcagcatt aaatgtatag      360
gaagcagtat tacaatcaaa atcagtttat ggcagccttt ccatgaatgc tcccatttca      420
gcatgcaaac taacctccac acgtccacac ctcccaccat aaacctgccc tatccccagc      480
ccacttccac gtacacaccc catgcaagtc ctggacttca ctataaataa ctgcccttca      540
tccccctctt cactcactca tc                                              562
```

<210> SEQ ID NO 20
<211> LENGTH: 537
<212> TYPE: DNA
<213> ORGANISM: Vitis vinifera cv. Merlot

<400> SEQUENCE: 20

```
gcttaatcca gttgaagagt gaaggttggg ccggagcctt acagcccaaa ttgagttggt       60
gggttggtgc tgagaggctt gtgttcaaag tccatatcca ttcgaaaaaa ttttgccctc      120
ttgtataagc ctcaggaatc tctttagcct ttaattaaac ctaaatccta ccaaaactgc      180
ccttcaaaat tattgctttg ttttaggtcc aagaatccta ataaggtct attttgaaac      240 attcctaatg gggtgggctt tgcttctcca aacagaagca tactacttgc tgttgatgag      300
catgtctgtc acctccaaaa aaaggacaag gtaactttaa ctgcagcatt aaatgtatag      360
gaagcagtat tacaatcaaa atcagtttat ggcagccttt ccatgaatgc tcccatttca      420
gcatgcaaac taacctccac acgtccacac ctcccaccat aaacctgccc tatccccagc      480
ccacttccac gtacacaccc catgcaagtc ctggacttca ctataaataa ctgccct        537
```

<210> SEQ ID NO 21
<211> LENGTH: 512
<212> TYPE: DNA
<213> ORGANISM: Vitis vinifera cv. Merlot

<400> SEQUENCE: 21

```
gcttaatcca gttgaagagt gaaggttggg ccggagcctt acagcccaaa ttgagttggt       60
gggttggtgc tgagaggctt gtgttcaaag tccatatcca ttcgaaaaaa ttttgccctc      120
ttgtataagc ctcaggaatc tctttagcct ttaattaaac ctaaatccta ccaaaactgc      180
ccttcaaaat tattgctttg ttttaggtcc aagaatccta ataaggtct attttgaaac      240 attcctaatg gggtgggctt tgcttctcca aacagaagca tactacttgc tgttgatgag      300
catgtctgtc acctccaaaa aaaggacaag gtaactttaa ctgcagcatt aaatgtatag      360
```

```
gaagcagtat tacaatcaaa atcagtttat ggcagccttt ccatgaatgc tcccatttca    420
gcatgcaaac taacctccac acgtccacac ctcccaccat aaacctgccc tatccccagc    480
ccacttccac gtacacaccc catgcaagtc ct                                  512
```

<210> SEQ ID NO 22
<211> LENGTH: 487
<212> TYPE: DNA
<213> ORGANISM: Vitis vinifera cv. Merlot

<400> SEQUENCE: 22

```
gcttaatcca gttgaagagt gaaggttggg ccggagcctt acagcccaaa ttgagttggt     60
gggttggtgc tgagaggctt gtgttcaaag tccatatcca ttcgaaaaaa ttttgccctc    120
ttgtataagc ctcaggaatc tctttagcct ttaattaaac ctaaatccta ccaaaactgc    180
ccttcaaaat tattgctttg ttttaggtcc aagaatccta ataaggtct attttgaaac     240 attcctaatg gggtgggctt tgcttctcca aacagaagca tactacttgc tgttgatgag    300
catgtctgtc acctccaaaa aaaggacaag gtaactttaa ctgcagcatt aaatgtatag    360
gaagcagtat tacaatcaaa atcagtttat ggcagccttt ccatgaatgc tcccatttca    420
gcatgcaaac taacctccac acgtccacac ctcccaccat aaacctgccc tatccccagc    480
ccacttc                                                              487
```

<210> SEQ ID NO 23
<211> LENGTH: 437
<212> TYPE: DNA
<213> ORGANISM: Vitis vinifera cv. Merlot

<400> SEQUENCE: 23

```
gcttaatcca gttgaagagt gaaggttggg ccggagcctt acagcccaaa ttgagttggt     60
gggttggtgc tgagaggctt gtgttcaaag tccatatcca ttcgaaaaaa ttttgccctc    120
ttgtataagc ctcaggaatc tctttagcct ttaattaaac ctaaatccta ccaaaactgc    180
ccttcaaaat tattgctttg ttttaggtcc aagaatccta ataaggtct attttgaaac     240 attcctaatg gggtgggctt tgcttctcca aacagaagca tactacttgc tgttgatgag    300
catgtctgtc acctccaaaa aaaggacaag gtaactttaa ctgcagcatt aaatgtatag    360
gaagcagtat tacaatcaaa atcagtttat ggcagccttt ccatgaatgc tcccatttca    420
gcatgcaaac taacctc                                                   437
```

<210> SEQ ID NO 24
<211> LENGTH: 387
<212> TYPE: DNA
<213> ORGANISM: Vitis vinifera cv. Merlot

<400> SEQUENCE: 24

```
gcttaatcca gttgaagagt gaaggttggg ccggagcctt acagcccaaa ttgagttggt     60
gggttggtgc tgagaggctt gtgttcaaag tccatatcca ttcgaaaaaa ttttgccctc    120
ttgtataagc ctcaggaatc tctttagcct ttaattaaac ctaaatccta ccaaaactgc    180
ccttcaaaat tattgctttg ttttaggtcc aagaatccta ataaggtct attttgaaac     240 attcctaatg gggtgggctt tgcttctcca aacagaagca tactacttgc tgttgatgag    300
catgtctgtc acctccaaaa aaaggacaag gtaactttaa ctgcagcatt aaatgtatag    360
gaagcagtat tacaatcaaa atcagtt                                        387
```

<210> SEQ ID NO 25
<211> LENGTH: 537
<212> TYPE: DNA
<213> ORGANISM: Vitis vinifera cv. Merlot

<400> SEQUENCE: 25

| | | | | | |
|---|---|---|---|---|---|
| ttgggccgga | gccttacagc | ccaaattgag | ttggtgggtt | ggtgctgaga | ggcttgtgtt | 60 |
| caaagtccat | atccattcga | aaaaattttg | ccctcttgta | taagcctcag | gaatctcttt | 120 |
| agcctttaat | taaacctaaa | tcctaccaaa | actgcccttc | aaaattattg | ctttgtttta | 180 |
| ggtccaagaa | tcctaaataa | ggtctatttt | gaaacattcc | taatggggtg | ggctttgctt | 240 |
| ctccaaacag | aagcatacta | cttgctgttg | atgagcatgt | ctgtcacctc | caaaaaagg | 300 |
| acaaggtaac | tttaactgca | gcattaaatg | tataggaagc | agtattacaa | tcaaaatcag | 360 |
| tttatggcag | cctttccatg | aatgctccca | tttcagcatg | caaactaacc | tccacacgtc | 420 |
| cacacctccc | accataaacc | tgccctatcc | ccagcccact | tccacgtaca | caccccatgc | 480 |
| aagtcctgga | cttcactata | aataactgcc | cttcatcccc | ctcttcactc | actcatc | 537 |

<210> SEQ ID NO 26
<211> LENGTH: 487
<212> TYPE: DNA
<213> ORGANISM: Vitis vinifera cv. Merlot

<400> SEQUENCE: 26

| | | | | | |
|---|---|---|---|---|---|
| ttgagttggt | gggttggtgc | tgagaggctt | gtgttcaaag | tccatatcca | ttcgaaaaaa | 60 |
| ttttgccctc | ttgtataagc | ctcaggaatc | tctttagcct | ttaattaaac | ctaaatccta | 120 |
| ccaaaactgc | ccttcaaaat | tattgctttg | ttttaggtcc | aagaatccta | aataaggtct | 180 |
| attttgaaac | attcctaatg | ggtgggctt | tgcttctcca | aacagaagca | tactacttgc | 240 |
| tgttgatgag | catgtctgtc | acctccaaaa | aaggacaag | gtaactttaa | ctgcagcatt | 300 |
| aaatgtatag | gaagcagtat | tacaatcaaa | atcagtttat | ggcagccttt | ccatgaatgc | 360 |
| tcccatttca | gcatgcaaac | taacctccac | acgtccacac | ctcccaccat | aaacctgccc | 420 |
| tatcccagc | ccacttccac | gtacacaccc | catgcaagtc | ctggacttca | ctataaataa | 480 |
| ctgccct | | | | | | 487 |

<210> SEQ ID NO 27
<211> LENGTH: 437
<212> TYPE: DNA
<213> ORGANISM: Vitis vinifera cv. Merlot

<400> SEQUENCE: 27

| | | | | | |
|---|---|---|---|---|---|
| ggcttgtgtt | caaagtccat | atccattcga | aaaaattttg | ccctcttgta | taagcctcag | 60 |
| gaatctcttt | agcctttaat | taaacctaaa | tcctaccaaa | actgcccttc | aaaattattg | 120 |
| ctttgtttta | ggtccaagaa | tcctaaataa | ggtctatttt | gaaacattcc | taatggggtg | 180 |
| ggctttgctt | ctccaaacag | aagcatacta | cttgctgttg | atgagcatgt | ctgtcacctc | 240 |
| caaaaaagg | acaaggtaac | tttaactgca | gcattaaatg | tataggaagc | agtattacaa | 300 |
| tcaaaatcag | tttatggcag | cctttccatg | aatgctccca | tttcagcatg | caaactaacc | 360 |
| tccacacgtc | cacacctccc | accataaacc | tgccctatcc | ccagcccact | tccacgtaca | 420 |
| caccccatgc | aagtcct | | | | | 437 |

<210> SEQ ID NO 28
<211> LENGTH: 387
<212> TYPE: DNA

```
<213> ORGANISM: Vitis vinifera cv. Merlot

<400> SEQUENCE: 28
ttcgaaaaaa ttttgccctc ttgtataagc ctcaggaatc tctttagcct ttaattaaac    60
ctaaatccta ccaaaactgc ccttcaaaat tattgctttg ttttaggtcc aagaatccta   120
aataaggtct attttgaaac attcctaatg gggtgggctt tgcttctcca aacagaagca   180
tactacttgc tgttgatgag catgtctgtc acctccaaaa aaaggacaag gtaactttaa   240
ctgcagcatt aaatgtatag gaagcagtat tacaatcaaa atcagtttat ggcagccttt   300
ccatgaatgc tcccatttca gcatgcaaac taacctccac acgtccacac ctcccaccat   360
aaacctgccc tatccccagc ccacttc                                       387

<210> SEQ ID NO 29
<211> LENGTH: 167
<212> TYPE: PRT
<213> ORGANISM: Vitis vinifera cv. Merlot

<400> SEQUENCE: 29
```

Met Ala Lys Leu Ser Ile Phe Ala Ala Thr Leu Leu Leu Leu Ala
1               5                   10                  15

Ile Ser Asn Ala Thr Ile Tyr Gln Thr Thr Val Ile Thr Arg Asp Asp
            20                  25                  30

Gly Ser Glu Phe Gly Gln Phe Gln Gly Ser Gln Ser Gln Arg Cys Arg
        35                  40                  45

Gln Gln Ile Gln Gly Gln Gln Phe Gln Gln Cys Glu Arg Tyr Ile Arg
    50                  55                  60

Gln Gln Ala Glu Gln Gln Gln Gly Gly Gln Gly Asp Val Leu Ile Leu
65                  70                  75                  80

Arg Gly Ile Arg Asn Gln Gln Gln Gln Glu Gln Gln Trp Leu Arg Gln
                85                  90                  95

Cys Cys Gln Ala Leu Gln Asn Met Asp Gln Gln Cys Gln Cys Glu Gly
            100                 105                 110

Leu Arg Gln Ile Val Gln Arg Gln Gln Gly Gln Gly Gln Gly Gln Gly
        115                 120                 125

Gln Gly Gln Gly Gln Gly Gln Arg Glu Gln Gln Gln Glu Met Met Gln
    130                 135                 140

Ile Ala Gln Lys Leu Pro Glu Arg Cys Gly Ser Gly Gln Ala Cys Gln
145                 150                 155                 160

Ser Met Gln Val Val Trp Phe
                165